(12) United States Patent
Lee et al.

(10) Patent No.: US 11,653,953 B2
(45) Date of Patent: May 23, 2023

(54) IMPLANT RECEIVERS AND CONNECTORS WITH GRIP GROOVES FOR ROD FIXATION

(71) Applicant: Medos International Sarl, Le Locle (CH)

(72) Inventors: Kevin Lee, Canton, MA (US); Samuel Jacobs, Acton, MA (US); Aubrey Ortiz, Boston, MA (US)

(73) Assignee: MEDOS INTERNATIONAL SARL, Le Locle (CH)

(*) Notice: Subject to any disclaimer, the term of this patent is extended or adjusted under 35 U.S.C. 154(b) by 185 days.

(21) Appl. No.: 16/599,902

(22) Filed: Oct. 11, 2019

(65) Prior Publication Data

US 2021/0106360 A1   Apr. 15, 2021

(51) Int. Cl.
*A61B 17/70* (2006.01)
*A61B 17/86* (2006.01)

(52) U.S. Cl.
CPC .......... *A61B 17/7034* (2013.01); *A61B 17/86* (2013.01)

(58) Field of Classification Search
CPC . A61B 17/7034; A61B 17/86; A61B 17/7049; A61B 17/7032; A61B 17/7035; A61B 17/7037
USPC .................................................. 606/250–279
See application file for complete search history.

(56) References Cited

U.S. PATENT DOCUMENTS

| | | | |
|---|---|---|---|
| 6,673,073 B1 * | 1/2004 | Schafer | A61B 17/7049 606/250 |
| 6,736,820 B2 | 5/2004 | Biedermann et al. | |
| 6,974,460 B2 | 12/2005 | Carbone et al. | |
| 7,008,423 B2 | 3/2006 | Assaker et al. | |
| 7,104,993 B2 | 9/2006 | Baynham et al. | |
| 7,179,261 B2 | 2/2007 | Sicvol et al. | |
| 7,485,132 B1 | 2/2009 | McBride et al. | |
| 7,585,299 B2 | 9/2009 | Rezach | |
| 7,803,174 B2 | 9/2010 | Denis et al. | |
| 8,016,862 B2 | 9/2011 | Felix et al. | |
| 8,414,617 B2 | 4/2013 | Young et al. | |
| 8,491,642 B2 | 7/2013 | Marino et al. | |
| 9,320,547 B2 | 4/2016 | Augostino | |
| 9,707,015 B2 | 7/2017 | Hirschl et al. | |
| 9,956,005 B2 | 5/2018 | Beyar et al. | |

(Continued)

OTHER PUBLICATIONS

International Search Report and Written Opinion for International Application No. PCT/IB2020/059555, dated Mar. 3, 2021 (11 pages).

*Primary Examiner* — Tessa M Matthews
*Assistant Examiner* — Tara Rose E Carter
(74) *Attorney, Agent, or Firm* — Barnes & Thornburg, LLP

(57) ABSTRACT

Implants with grip grooves are disclosed herein. In some embodiments, an implant includes a rod-receiving recess defining a rod axis where an inner surface of the rod-receiving recess defines two grip grooves extending parallel to each other and the rod axis. Each grip groove defines two edges where the grip groove intersects the inner surface, the four edges of the two grip grooves together defining a circular radius about the rod axis. The implant includes a retaining member configured to move with respect to the body to apply a force against a rod that is perpendicular to the rod axis, the force engaging the rod against the four edges of the grip grooves, where the engagement of the four edges of the grip grooves against the rod restrains rotational movement of the rod about the rod axis.

19 Claims, 36 Drawing Sheets

(56) References Cited

U.S. PATENT DOCUMENTS

| | | |
|---|---|---|
| 9,974,570 B2 | 5/2018 | Black |
| 10,098,671 B2 | 10/2018 | Augostino |
| 10,238,432 B2* | 3/2019 | Carruth .............. A61B 17/7032 |
| 10,966,761 B2* | 4/2021 | Lee .................... A61B 17/7052 |
| 2005/0277927 A1* | 12/2005 | Guenther ........... A61B 17/7037 |
| | | 606/301 |
| 2008/0051780 A1 | 2/2008 | Vaidya et al. |
| 2008/0312692 A1* | 12/2008 | Brennan ............ A61B 17/7005 |
| | | 606/301 |
| 2010/0114174 A1 | 5/2010 | Jones et al. |
| 2011/0087287 A1* | 4/2011 | Reeder, Jr. ........... A61B 17/705 |
| | | 606/250 |
| 2011/0288599 A1 | 11/2011 | Michielli et al. |
| 2012/0296335 A1 | 11/2012 | Mullaney |
| 2013/0085536 A1* | 4/2013 | Biedermann ...... A61B 17/7035 |
| | | 606/308 |
| 2016/0166289 A1* | 6/2016 | Alsup ................. A61B 17/705 |
| | | 606/253 |
| 2017/0020577 A1 | 1/2017 | Loch et al. |
| 2017/0333087 A1 | 11/2017 | Lee et al. |
| 2017/0333088 A1* | 11/2017 | Lee .................... A61B 17/7049 |
| 2018/0228518 A1 | 8/2018 | Carruth et al. |
| 2018/0280062 A1* | 10/2018 | Lee ..................... A61B 17/705 |

* cited by examiner (A-A)

IMPLANT RECEIVERS AND CONNECTORS WITH GRIP GROOVES FOR ROD FIXATION

FIELD

Implant receivers and connectors with grip grooves for improved rod fixation are disclosed herein.

BACKGROUND

Fixation systems can be used in orthopedic surgery to maintain a desired spatial relationship between multiple bones or bone fragments. For example, various conditions of the spine, such as fractures, deformities, and degenerative disorders, can be treated by attaching a spinal fixation system to one or more vertebrae. Such systems typically include a spinal fixation element, such as a rigid or flexible rod or plate that is coupled to the vertebrae by attaching the element to various anchoring devices, such as screws, hooks, or wires. Once installed, the fixation system holds the vertebrae in a desired position until healing or spinal fusion can occur, or for some other period of time.

In screw and rod spinal fixation constructs, stability of the implanted construct is crucial in allowing the body to accomplish bony fusion through the operative levels. Instability of, or motion within an implanted construct can result in a pseudoarthrosis, a "non-union" where new bone formation fails to take over loads experienced by the screw and rod construct. Where there is too much motion allowed between instrumented vertebrae, growth activity is hindered; new bone cannot fuse between two bodies that are constantly moving relative to one another. To solve this problem and provide stable fixation, polyaxial screw-heads, rod to rod, and screw-head to rod connectors all need to hold securely to the rod. These implants must resist motion relative to the longitudinal rods in the construct; this includes the rod sliding, rotating, or pulling away from the connector or bone screw.

There are many instances in which it may be desirable to connect multiple implants to each other. For example, some revision surgeries involve extending a previously-installed construct to additional vertebral levels by coupling a newly-installed spinal rod to a previously-installed rod. In addition, with vertebral implants or constructs fixated in the cervical and thoracic regions of the spine, a rod-to-rod connector can be used to bridge the transition between the constructs or implants in the cervical and thoracic regions. In this example, and in other transition regions, torsional slip between the implants on the rod or rods connecting them to each other is a serious risk, which can be caused by routine and repetitive movements, for example the patient twisting their head. By way of further example, aspects of the patient's anatomy, the surgical technique used, or the desired correction may require that multiple spinal rods be connected to one another. As yet another example, coupling multiple rods to one another can improve the overall strength and stability of an implanted construct.

There can be various difficulties associated with connecting multiple implants to each other. The available space for the implanted construct can often be very limited, particularly in the cervical area of the spine. Also, manipulating and handling these relatively small implants in the surgical wound may be challenging or cumbersome for the surgeon. There is a continual need for improved implant connectors and related methods.

SUMMARY

Certain examples of the present disclosure include an implant with a body having a rod-receiving recess, where the body has first and second sides defining openings to the rod-receiving recess and the rod-receiving recess defines a central longitudinal rod axis extending between the openings of the first and second sides. At least a portion of the rod-receiving recess can be formed by an inner surface of the implant, with the inner surface defining two grip grooves extending parallel to each other and the central longitudinal rod axis. Each grip groove defines two edges where the grip groove intersects the inner surface, the four edges of the two grip grooves together defining a circular radius about the central longitudinal rod axis. The implant also includes a retaining member configured to move with respect to the body, exert a force against a rod in the rod-receiving recess that can be perpendicular to the central longitudinal rod axis, and engage the rod against the four edges of the two grip grooves. Additionally, engagement of the four edges of the grip grooves against the rod can restrain rotational movement of the rod about the central longitudinal rod axis.

In some examples, the rod-receiving recess defines a gap between the two grip grooves sized and positioned to allow the force against the rod in the rod-receiving recess to permit deflection of one or both of the edges and the rod where the edges engage the rod, the deflection causing movement of the rod into the gap. The inner surface of the rod-receiving recess between the two grip grooves can be positioned a distance away from the central longitudinal rod axis that is larger than a radius of the rod.

In some examples, the implant includes a compression member disposed in a cavity formed in the body, with the compression member having an inner surface defining at least a portion of the rod-receiving recess, with an inner surface of the compression member having the two grip grooves formed therein. In some examples, the grip grooves extend along an entire length of the inner surface of the rod-receiving recess in the direction of the central longitudinal rod axis. In some examples, the grip grooves are positioned opposite the retaining member with respect to the central longitudinal rod axis.

The rod-receiving recess can define an open end sized to accept the rod and a closed end sized to contact the rod, where the grip grooves are arranged symmetrically about an axis extending from the open end to the closed end. The body of the implant can define the inner surface forming the rod-receiving recess. In some examples, the intersection between the grip grooves and the inner surface defines sharp edges.

The inner surface can define a groove intersecting at least one grip groove, the intersection of the groove segmenting the edges of the at least one grip groove and defining four corners for resisting translation of the rod along the central longitudinal rod axis when the rod is engaged with the edges. In some examples, the groove intersecting at least one grip groove is oriented perpendicular to the grip grooves.

The grip grooves can be formed by protrusions extending from the inner surface. In some examples, at least one grip groove defines an inner surface having formed therein one or more protrusions, the one or more protrusions extending to edges arranged to contact the rod when the rod is engaged with the edges of the grip grooves.

In some examples, the implant includes a connector and the rod-receiving recess is a first rod-receiving recces, the body defining a second rod-receiving recesses, with one or both of the first and second rod-receiving recesses having the two grip grooves. The body has proximal and distal ends that define a proximal-distal axis extending therebetween, with the retaining member slidably disposed within a tunnel formed in the body and configured to translate with respect to the body along a rod pusher axis.

In some examples, the second rod-receiving recess is defined by a pair of spaced apart arms of the body. The first rod-receiving recess can be open in a distal direction and the second rod-receiving recess can be open in a proximal direction. The rod pusher axis can be substantially perpendicular to the proximal-distal axis. In some examples, the implant further includes a set screw threadably received in the body to lock a first rod within the first rod-receiving recess and to lock a second rod within the second rod-receiving recess.

The implant can include a bone anchor assembly, with the body having a receiver member of the bone anchor assembly and the retaining member having a set screw or locking element.

Another example of the present disclosure is an implant having a body having a rod-receiving recess, a grip insert configured to be positioned in an open end of the receiving recess, and a retaining member configured to move with respect to the body. The body has first and second sides defining openings to the rod-receiving recess and the rod-receiving recess defines a central longitudinal rod axis extending between the openings of the first and second sides. The grip insert has an inner surface for contacting a rod disposed in the rod-receiving recess, with the inner surface defining two grip grooves extending parallel to each other and the central longitudinal rod axis, where each grip groove defines two edges where the grip groove intersects the inner surface and the four edges of the two grip grooves together defining a circular radius about the central longitudinal rod axis. The retaining member can be configured to exert a force against a rod in the rod-receiving recess and engage the four edges of the grip against the rod, where the engagement of the four edges of the grip grooves against the rod serves to restrain rotational movement of the rod about the central longitudinal rod axis.

Any of the features or variations described above can be applied to any particular example of the present disclosure in a number of different combinations. The absence of explicit recitation of any particular combination is due solely to the avoidance of repetition in this summary.

BRIEF DESCRIPTION OF THE DRAWINGS

FIG. 2I is a side view of the connector of FIG. 2A coupled to first and second spinal rods;

DETAILED DESCRIPTION

Figure 1A:
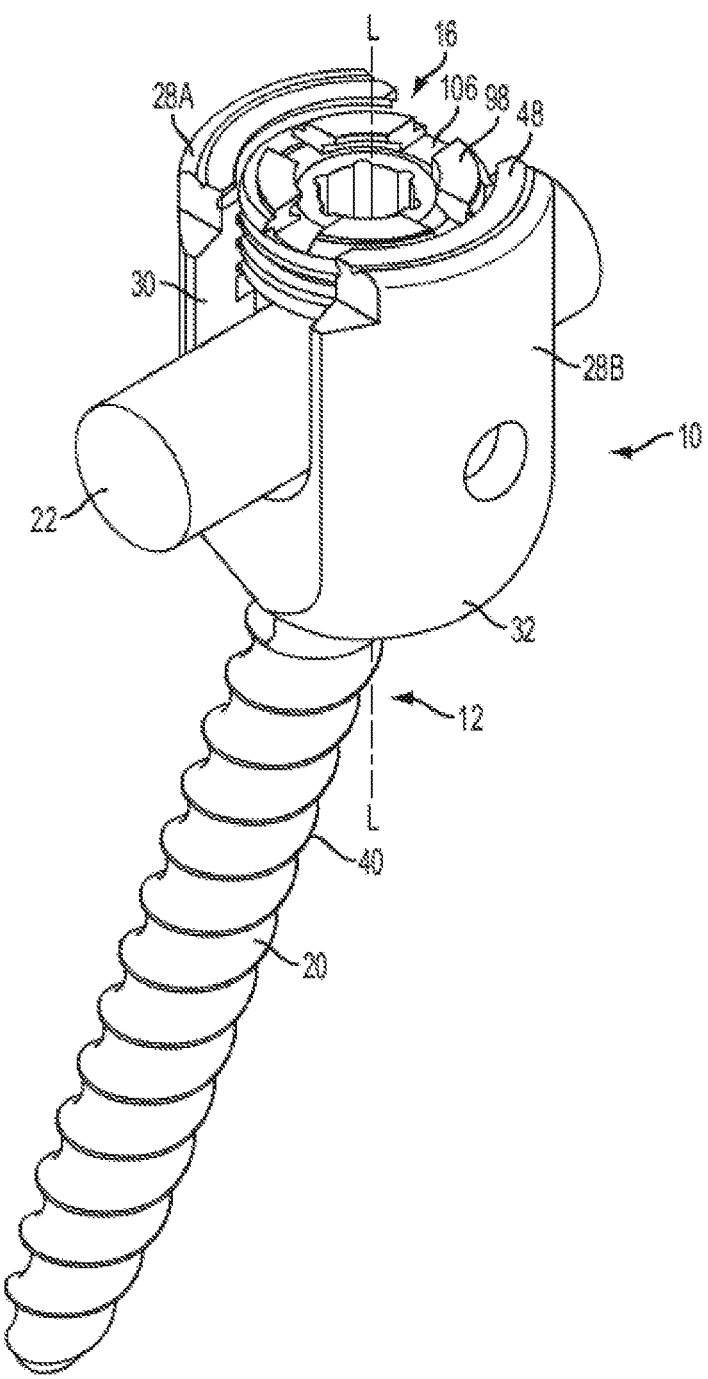
FIG. 1A is a perspective view of a prior art bone anchor assembly.

Implants with grip grooves and related methods are disclosed herein. The implants can include connectors and receiver members of bone anchor assemblies. In some examples, a connector can include a low-profile portion to facilitate use of the connector in surgical applications where space is limited. In some embodiments, a connector can include a biased rod-pusher to allow the connector to "snap" onto a rod and/or to "drag" against the rod, e.g., for provisional positioning of the connector prior to locking.

Certain aspects of the present disclosure provide for increased torsional gripping capacity of an implant on a rod. One example presented is a rod-to-rod connector, but the feature may be applied to various spinal implants such as screw heads of bone anchor assemblies. Aspects of the present disclosure include single or multiple longitudinal grooves cut in the rod slot of an implant that add extra lines of contact between the connector and the rod. In operation, when locked, a very small portion of the cross-sectional rod perimeter is wedged into the groove, causing both edges where the groove cut begins to press into the rod. Even if the rod tangency is not perfectly located relative to this groove, the groove provides an edge, rather than a flat face, to grind against the rod and prevent further rotation should rotation begin to occur from forces exerted upon the rod or connector. This micro-shearing of the material is the principle of increasing torsional gripping capacity.

Alternatively, these grip grooves can be on the surface of the rod instead of the connector, screw head, or receiving implant. In addition, the semi-circular grip grooves can be other geometries, such as rectangular, right angle or other angles, trapezoidal, etc.

A variation of the grip groove to increase the axial slip (longitudinal rod sliding) gripping capacity is to have the grooves in a circumferential orientation relative to the rod. The longitudinal and the circumferential grip grooves can also be combined to increase torsional and axial resistance. The resulting features may resemble pegs or corners.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

FIGS. 1A-1D illustrate a prior art bone anchor assembly 10 including a bone anchor 12, a receiver member 14 for receiving a spinal fixation element, such as a spinal rod 22, to be coupled to the bone anchor 12, and a closure mechanism 16 to capture a spinal fixation element within the receiver member 14 and fix the spinal fixation element with respect to the receiver member 14. The bone anchor 12 includes a proximal head 18 and a distal shaft 20 configured to engage bone. The receiver member 14 has a proximal end 26 having a pair of spaced apart arms 28A, 28B defining a recess 30 therebetween and a distal end 32 having an inner surface 35 for polyaxially seating the proximal head 18 of the bone anchor 12 and distal end surface 34 defining an opening through which at least a portion of the bone anchor 12 extends. The closure mechanism 16 can be positionable between and can engage the arms 28A, 28B to capture a spinal fixation element, e.g., a spinal rod 22, within the receiver member 14 and fix the spinal fixation element with respect to the receiver member 14.

The proximal head 18 of the bone anchor 12 is generally in the shape of a truncated sphere having a planar proximal surface 36 and an approximately spherically-shaped distal surface 38. The illustrated bone anchor assembly is a polyaxial bone anchor designed for posterior implantation in the pedicle or lateral mass of a vertebra. The proximal head 18 of the bone anchor 12 engages the distal end 32 of the receiver member 14 in a ball and socket like arrangement in which the proximal head 18 the distal shaft 20 can pivot relative to the receiver member 14. The distal surface 38 of the proximal head 18 of the bone anchor 12 and a mating surface within the distal end 32 of the receiver member 14 can have any shape that facilitates this arrangement, including, for example, spherical (as illustrated), toroidal, conical, frustoconical, and any combinations of these shapes.

The distal shaft 20 of the bone anchor 12 can be configured to engage bone and, in the illustrated embodiment, includes an external bone engaging thread 40. The thread form for the distal shaft 20, including the number of threads, the pitch, the major and minor diameters, and the thread shape, can be selected to facilitate connection with bone. Exemplary thread forms are disclosed in U.S. Patent Application Publication No. 2011/0288599, filed on May 18, 2011, and in U.S. Provisional Patent Application Ser. No. 61/527,389, filed Aug. 25, 2011, both of which are incorporated herein by reference. The distal shaft 20 can also include other structures for engaging bone, including a hook. The distal shaft 20 of the bone anchor 12 can be cannulated, having a central passage or cannula extending the length of the bone anchor to facilitate delivery of the bone anchor over a guide wire in, for example, minimally-invasive procedures. Other components of the bone anchor assembly, including, for example, the closure member 16, the receiver member 14, and the compression member 60 (discussed below) can be cannulated or otherwise have an opening to permit delivery over a guide wire or to permit the insertion of a driver instrument to manipulate the bone anchor. The distal shaft 20 can also include one or more sidewall openings or fenestrations that communicate with the cannula to permit bone in-growth or to permit the dispensing of bone cement or other materials through the bone anchor 12. The sidewall openings can extend radially from the cannula through the sidewall of the distal shaft 20. Exemplary systems for delivering bone cement to the bone anchor assembly 10 and alternative bone anchor configurations for facilitating cement delivery are described in U.S. Patent Application Publication No. 2010/0114174, filed on Oct. 29, 2009, which is hereby incorporated herein by reference. The distal shaft 20 of the bone anchor 12 can also be coated with materials to permit bone growth, such as, for example, hydroxyl apatite, and the bone anchor assembly 10 can be coated partially or entirely with anti-infective materials, such as, for example, triclosan.

The proximal end 26 of the receiver member 14 includes a pair of spaced apart arms 28A, 28B defining a U-shaped recess 30 therebetween for receiving a spinal fixation element, e.g., a spinal rod 22. Each of the arms 28A, 28B can extend from the distal end 32 of the receiver member 14 to a free end. The outer surfaces of each of the arms 28A, 28B can include a feature, such as a recess, dimple, notch, projection, or the like, to facilitate connection of the receiver member 14 to instruments. For example, the outer surface of each arm 28A, 28B can include an arcuate groove at the respective free end of the arms. Such grooves are described in more detail in U.S. Pat. No. 7,179,261, issued on Feb. 20, 2007, which is hereby incorporated herein by reference. At least a portion of the proximal end surface 48 of the receiver member 12 defines a plane Y. The receiver member 14 has a central longitudinal axis L.

The distal end 32 of the receiver member 14 includes a distal end surface 34 which is generally annular in shape defining a circular opening through which at least a portion of the bone anchor 12 extends. For example, the distal shaft 20 of the bone anchor 12 can extend through the opening. At least a portion of the distal end surface 34 defines a plane X.

The bone anchor 12 can be selectively fixed relative to the receiver member 14. Prior to fixation, the bone anchor 12 is movable relative to the receiver member 14 within a cone of angulation generally defined by the geometry of the distal end 32 of the receiver member and the proximal head 18 of the bone anchor 12. The illustrated bone anchor is a favored-angle polyaxial screw in which the cone of angulation is biased in one direction. In this manner, the bone anchor 12 is movable relative to the receiver member 14 in at least a first direction, indicated by arrow A in FIG. 1D, at a first angle C relative to the central longitudinal axis L of the receiver member 14. The bone anchor 12 is also movable in at least a second direction, indicated by arrow B in FIG. 1D, at a second angle D relative to the longitudinal axis L. The first angle C is greater than the second angle D and, thus, the shaft 20 of the bone anchor 12 is movable more in the direction indicated by arrow A than in the direction indicated by arrow B. The distal shaft 20 of the bone anchor 12 defines a neutral axis 48 with respect to the receiver member 14. The neutral axis 48 can be perpendicular to the plane X defined by the distal end surface 34 and intersects the center point of the opening in the distal end surface 34 through which the distal shaft 20 of the bone anchor 12 extends. The neutral axis 48 can be oriented at an angle to the central longitudinal axis L of the receiver member 14. The plane Y defined by at least a portion of the proximal end surface 48 of the receiver member 14 intersects the plane X defined by at least a portion of the distal end surface 34 of the receiver member 12. The proximal end 26 of the receiver member 14 can include a proximal first bore 50 coaxial with a first central longitudinal axis N (which is coincident with longitudinal axis L) and a distal second bore 52 coaxial with a second central longitudinal axis M (which is coincident with the neutral axis 48) and the first central longitudinal axis N and second central longitudinal axis M can intersect one another. The angle between the plane X and the plane Y and the angle between the axis L and the axis M can be selected to provide the desired degree of biased angulation. Examples of favored angled polyaxial screws are described in more detail in U.S. Pat. No. 6,974,460, issued on Dec. 13, 2005, and in U.S. Pat. No. 6,736,820, issued on May 18, 2004, both of which are hereby incorporated herein by reference. Alternatively, the bone anchor assembly can be a conventional (non-biased) polyaxial screw in which the bone anchor pivots in the same amount in every direction and has a neutral axis that is coincident with the central longitudinal axis L of the receiver member.

The spinal fixation element, e.g., the spinal rod 22, can either directly contact the proximal head 18 of the bone anchor 12 or can contact an intermediate element, e.g., a compression member 60. The compression member 60 can be positioned within the receiver member 14 and interposed between the spinal rod 22 and the proximal head 18 of the bone anchor 12 to compress the distal outer surface 38 of the proximal head 18 into direct, fixed engagement with the distal inner surface of the receiver member 14. A proximal portion of the compression member 60 can include a pair of spaced apart arms 62A and 62B defining a U-shaped seat 64 for receiving the spinal rod 22. A distal portion of the compression member 60 can include a sidewall having an inner cylindrical surface 67 that is connected to an outer cylindrical surface 68 by a distal-facing surface 66, At least a portion of the distal surface 66 of the compression member 60 can be shaped as a negative of the proximal portion 18 of the bone anchor 20, against which the distal surface 66 abuts when the compression member 60 is fully inserted into the receiver member 14. Thus, when the shaft 20 of the bone anchor 12 is oriented along the longitudinal axis L, the contact area between the distal surface 66 of the compression member 60 and the proximal head 18 is maximized. Where the angle of the shaft 20 with respect to the longitudinal axis L is not zero, however, the contact area between the distal surface 66 of the compression member 60 and the head 18 can be reduced, thus increasing a risk of slippage of the bone anchor 12 with respect to the receiver member 14.

Figure 1B:
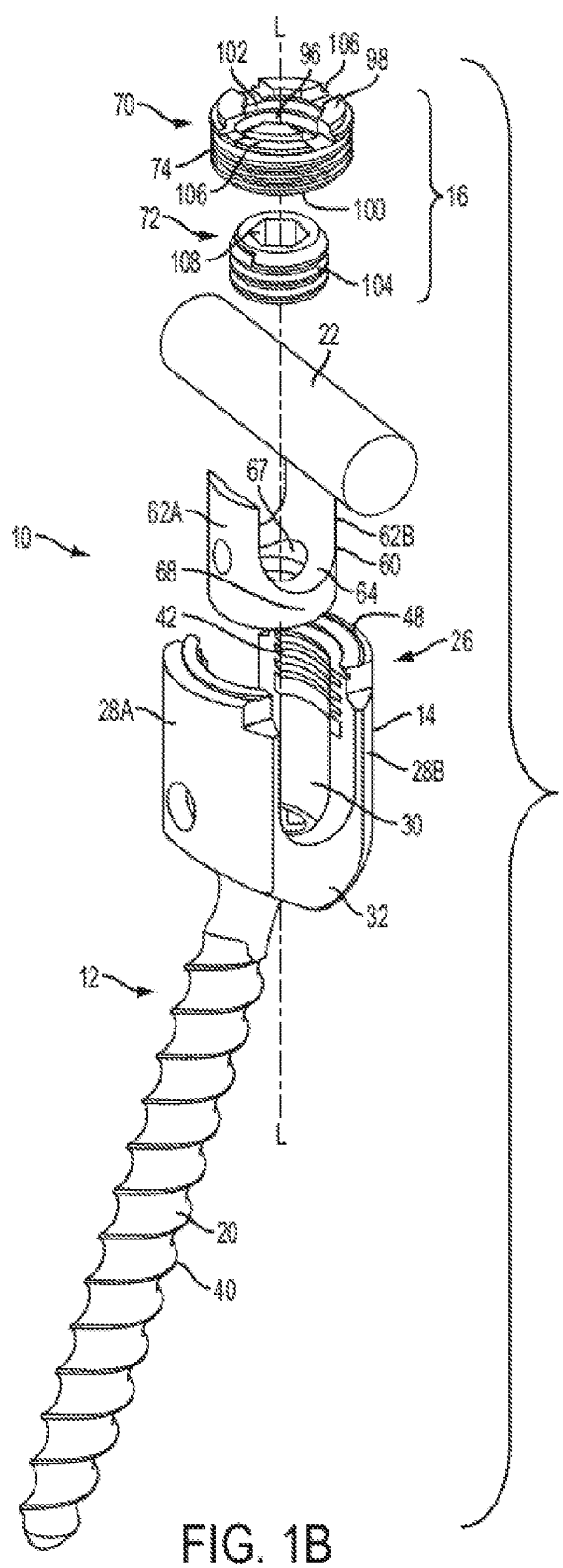
FIG. 1B is an exploded view of the bone anchor assembly of FIG. 1A.
Figure 1C:
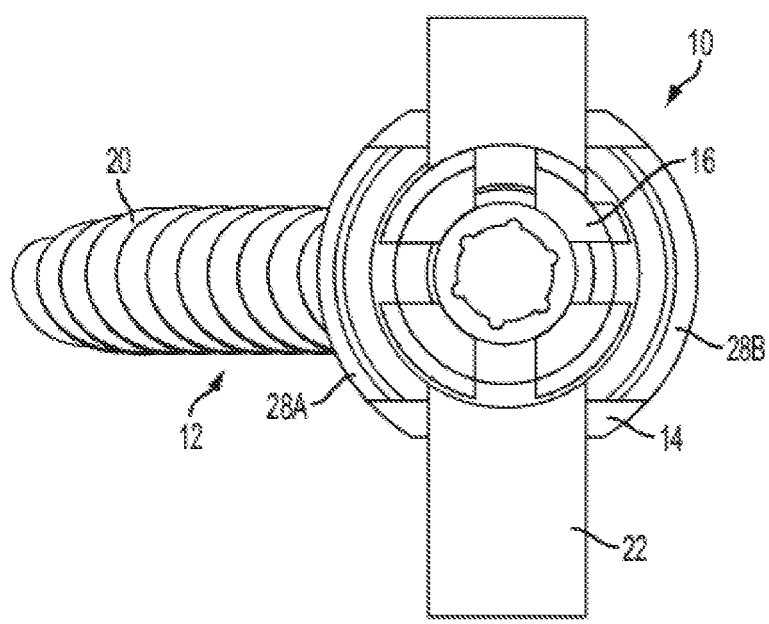
FIG. 1C is a top view of the bone anchor assembly of FIG. 1A.
Figure 1D:
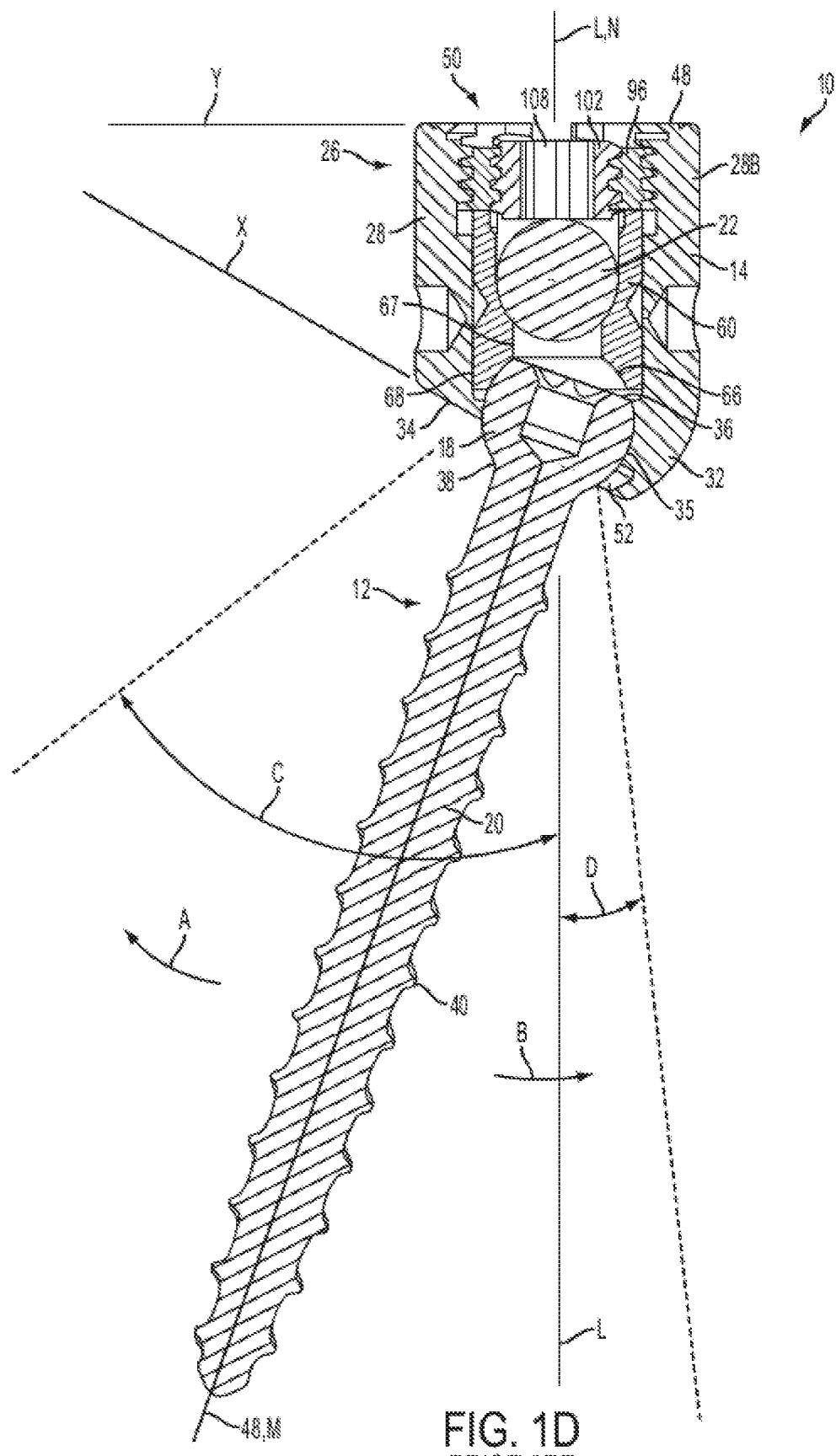
FIG. 1D is a cross-sectional view of the bone anchor assembly of FIG. 1A.

As best seen in FIG. 1B, the compression member 60 is configured to slide freely along the longitudinal axis L within the recess 30 of the receiver member 14. To secure the compression member 60 within the receiver member 14, the compression member 60 can be configured to mate with the receiver member, for example by mechanically deforming a portion of the compression member 60 against the receiver member 14. In the illustrated embodiment, opposing bores formed in the arms 62A, 62B of the compression member 60 are aligned with bores formed in the arms 62A, 62B of the receiver member 14, such that opposing pins can be inserted through the passageways defined by the bores to compress or "swage" the compression member 60 against the receiver member 14. The swaging process can prevent subsequent removal of the compression member 60 from the receiver member 14.

The proximal end 26 of the receiver member 14 can be configured to receive a closure mechanism 16 positionable between and engaging the arms 28A, 28B of the receiver member 14. The closure mechanism 16 can be configured to capture a spinal fixation element, e.g., a spinal rod 22, within the receiver member 14, to fix the spinal rod 22 relative to the receiver member 14, and to fix the bone anchor 12 relative to the receiver member 14. The closure mechanism 16 can be a single set screw having an outer thread for engaging an inner thread 42 provided on the arms 28A, 28B of the receiver member 14. In the illustrated embodiment, however, the closure mechanism 16 comprises an outer set screw 70 positionable between and engaging the arms 28A, 28B of the receiver member 14 and an inner set screw 72 positionable within the outer set screw 70. The outer set screw 70 is operable to act on the compression member 60 to fix the bone anchor 12 relative to the receiver member 14. The inner set screw 72 is operable to act on the spinal rod 22 to fix the spinal rod 22 relative to the receiver member 14. In this manner, the closure mechanism 16 permits the bone anchor 12 to be fixed relative to the receiver member 14 independently of the spinal rod 22 being fixed to the receiver member 14. In particular, the outer set screw 70 can engage the proximal end surfaces of the arms 62A, 62B of the compression member 60 to force the distal-facing surface 66 of the compression member 60 into contact with the proximal head 18 of bone anchor 12, which in turn forces the distal surface 38 of the proximal head 18 into fixed engagement with the distal inner surface of the receiver member 14. The inner set screw 72 can engage the spinal rod 22 to force the spinal rod 22 into fixed engagement with the rod seat 64 of the compression member 60.

The outer set screw 70 includes a first outer thread 74 for engaging a complementary inner thread 42 on the arms 28A, 28B of the receiver member 14. The outer set screw 74 includes a central passage 96 from a top surface 98 of the outer set screw 74 to a bottom surface 100 of the outer set screw 74 for receiving the inner set screw 72. The central passage 96 can includes an inner thread 102 for engaging a complementary outer thread 104 on the inner set screw 72. The thread form for the inner thread 102 and the outer thread 104, including the number of threads, the pitch, major and minor diameter, and thread shape, can be selected to facilitate connection between the components and transfer of the desired axial tightening force. The top surface 98 of the outer set screw 74 can have one or more drive features to facilitate rotation and advancement of the outer set screw 74 relative to the receiver member 14. The illustrated outer set screw 74 includes drive features in the form of a plurality of cut-outs 106 spaced-apart about the perimeter of the top surface 98. The inner set screw 104 can include drive features for receiving an instrument to rotate and advance the inner set screw 72 relative to the outer set screw 74. The illustrated inner set screw 104 includes drive features in the form of a central passage 108 having a plurality of spaced apart, longitudinally oriented cut-outs for engaging complementary features on an instrument.

The bone anchor assembly 10 can be used with a spinal fixation element such as rigid spinal rod 22. The various components of the bone anchor assemblies disclosed herein, as well as the spinal rod 22, can be constructed from various materials, including titanium, titanium alloys, stainless steel, cobalt chrome, PEEK, or other materials suitable for rigid fixation. In other embodiments, the spinal fixation element can be a dynamic stabilization member that allows controlled mobility between the instrumented vertebrae.

In use, bone can be prepared to receive the bone anchor assembly 10, generally by drilling a hole in the bone which is sized appropriately to receive the bone anchor 12. If not already completed, the bone anchor assembly 10 can be assembled, which can include assembling the bone anchor 12 and the receiver member 14, so that the distal shaft 20 extends through the opening in the distal end 32 of the receiver member 14 and the proximal head 18 of the bone anchor 12 is received in the distal end 32 of the receiver member 14. A driver tool can be fitted with the bone anchor 12 to drive the bone anchor 12 into the prepared hole in the bone. The compression member 60 can be positioned within the receiver member 14 such that the arms 62A, 62B of the compression member are aligned with the arms 28A, 28B of the receiver member 14 and the lower surface of the compression member 14 is in contact with the proximal head 18 of the bone anchor 12. A spinal fixation element, e.g., the spinal rod 22, can be located in the recess 30 of the receiver member 14. The closure mechanism 16 can be engaged with the inner thread 42 provided on the arms 28A, 28B of the receiver member 14. A torsional force can be applied to the outer set screw 70 to move it within the recess 30 using a tool which can engage the plurality of cut-outs 106 in the upper facing surface of the outer set screw 70, so as to force the compression member 60 onto the proximal head 18 of the bone anchor 12. Torsional forces can then be applied to the inner set screw 72 to move it relative to the outer set screw 70 so that it contacts the spinal rod 22 and can, for example, fix the spinal rod 22 relative to the receiver member 14 and the bone anchor 12.

One or more embodiments of inventive bone anchor assemblies are described below.

Except as indicated below, the structure, operation, and use of these embodiments is similar or identical to that of the bone anchor assembly 10 described above. Accordingly, a detailed description of said structure, operation, and use is omitted here for the sake of brevity. FIGS. 3A-12 show various embodiments of rod-receiving recesses similar to the recesses formed by the receiver member 14 and/or the compression member 60 shown in FIG. 1B but with gripping recesses or features formed on the inner surface of the rod-receiving recess for gripping a cylindrical rod 22 with greater friction as compared with the receiver member 14 and/or the compression member 60 of the bone anchor shown in FIG. 1B. The rod-receiving recesses shown in FIGS. 3A-12 can be used with the bone anchor assembly shown in FIGS. 1A-1D, or with various other bone anchor assemblies known in the art. FIGS. 8C and 8D show rod-receiving recesses with locking members arranged to compress an insert having gripping recesses or features formed therein against the cylindrical rod 22. The inserts shown in FIGS. 8C and 8D can be used with the bone anchor assembly shown in FIGS. 1A-1D, or with various other bone anchor assemblies known in the art, and can be urged against the cylindrical rod 22 by a locking mechanism such as the outer set screw 70 or inner set screw 72 shown in FIGS. 1A-1D.

FIGS. 2A-2L illustrate a prior art connector 200 with a traditional configuration for securing a rod to the connector 200. As shown, the connector 200 can include a body 202 that defines first and second rod-receiving recesses 204, 206, a rod pusher 208, a bias element or spring wire 212, and a locking element or set screw 216. The rod pusher 208 can be configured to translate laterally within the body 202, and can be biased by the spring wire 212 in a direction that urges the rod pusher into a first rod R1 disposed in the first rod-receiving recess 204. The set screw 216 can be tightened to lock the connector 200 to both the first rod R1 and to a second rod R2 disposed in the second rod-receiving recess 206. The illustrated connector 200 can thus allow for one-step locking of first and second rods R1, R2 to the connector. The connector 200 can include one or more low-profile portions to facilitate use in tight spaces. For example, the first rod-receiving recess 204 can be formed in a portion of the connector body 202 having a reduced-profile, e.g., to fit between bone anchors implanted in adjacent levels of the cervical spine.

The body 202 can include proximal and distal ends 202p, 202d that define a proximal-distal axis A1. The proximal end 202p of the body 202 can include a pair of spaced apart arms 218, 220 that define the second rod-receiving recess 206 therebetween. A rod R2 disposed in the second rod-receiving recess 206 can have a central longitudinal rod axis A2. The second rod-receiving recess 206 can be open in a proximal direction, such that a rod R2 can be inserted into the recess by moving the rod distally with respect to the connector 200. Each of the arms 218, 220 can extend from the distal portion 202d of the body 202 to a free end. The outer surfaces of each of the arms 218, 220 can include a feature (not shown), such as a recess, dimple, notch, projection, or the like, to facilitate coupling of the connector 200 to various instruments. For example, the outer surface of each arm 218, 220 can include an arcuate groove at the respective free end of the arms for attaching the connector 200 to an extension tower or retractor. The arms 218, 220 can include or can be coupled to extension or reduction tabs (not shown) that extend proximally from the body 202 to functionally extend the length of the arms 218, 220. The extension tabs can facilitate insertion and reduction of a rod or other implant, as well as insertion and locking of the set screw 216. The extension tabs can be configured to break away or otherwise be separated from the arms 218, 220. The inner surfaces of each of the arms 218, 220 can be configured to mate with the set screw 216. For example, the inner surfaces of the arms 218, 220 can include threads that correspond to external threads formed on the set screw 216. Accordingly, rotation of the set screw 216 with respect to the body 202 about the axis A1 can be effective to translate the set screw with respect to the body axially along the axis A1.

The distal end 202d of the body 202 can define a tunnel 228 in which the rod pusher 208 can be disposed. The tunnel 228 can extend along a rod pusher axis A3 between the second rod-receiving recess 206 and the first rod-receiving recess 204. The rod pusher 208 can be configured to translate within the tunnel 228 along the axis A3. The axis A3 can be perpendicular or substantially perpendicular to the axis A1. The axis A3 can also be perpendicular or substantially perpendicular to the axis A2. The tunnel 228 can have a shape that is substantially a negative of the exterior shape of the rod pusher 208. A through-bore 224 can be formed in the body 202 such that the through-bore intersects with the tunnel 228. The through-bore 224 can extend perpendicular or substantially perpendicular to the axis A3. The through-bore 224 can be sized to receive the spring wire 212 therein, as described further below. The through-bore 224 can be open at both ends or one or both ends can be closed.

The body 202 can include a cantilevered wing portion 230 that defines the first rod-receiving recess 204. A rod R1 disposed in the first rod-receiving recess 204 can have a central longitudinal rod axis A4. The axis A4 can be parallel to the axis A2 as shown, or can be perpendicular or obliquely angled with respect to the axis A2. The wing portion 230 can extend radially-outward from the second arm 220 of the body 202. The wing portion 230 can have a width 230W and a height 230H. A ratio of the width 230W to the diameter of the first rod-receiving recess 204 (or of a rod R1 disposed therein) can be less than about 1.5:1, less than about 2:1, and/or less than about 3:1. A ratio of the height 230H to the diameter of the first rod-receiving recess 204 (or of a rod R1 disposed therein) can be less than about 0.5:1, less than about 1:1, and/or less than about 2:1. The height 230H can be less than about 5 mm, less than about 4 mm, and/or less than about 3 mm. The first rod-receiving recess 204 can be open in a distal direction such that a rod R1 can be inserted into the recess by moving the connector 200 distally with respect to the rod. The first rod-receiving recess 204 can be open in a proximal direction, e.g., by flipping the wing portion 230 and forming it such that it extends from a distal portion of the body 202, or in a lateral direction.

As noted above, the rod pusher 208 can be slidably disposed within the tunnel 228 of the body 202 and can be configured to translate with respect to the body along the axis A3. The rod pusher 208 can include a first bearing surface 244A configured to contact and bear against a first rod R1 disposed in the first rod-receiving recess 204. The bearing surface 244A can extend at an oblique angle with respect to a longitudinal axis of the rod pusher 208 such that the bearing surface is ramped. The bearing surface 244A can be planar as shown, or can be convex, concave, pointed, sharpened, etc. For example, the bearing surface 244A can be concave and can define a section of a cylinder, such that the bearing surface matches or approximates the contour of a cylindrical rod R1 disposed in the first rod-receiving recess 204. The rod pusher 208 can include a second bearing surface 244B configured to contact and bear against a second rod R2 disposed in the second rod-receiving recess 206. The bearing surface 244B can extend at an oblique angle with respect to a longitudinal axis of the rod pusher 208 such that the bearing surface is ramped. The bearing surface 244B can be planar as shown, or can be convex, concave, pointed, sharpened, etc. For example, the bearing surface 244B can be concave and can define a section of a cylinder, such that the bearing surface matches or approximates the contour of a cylindrical rod R2 disposed in the second rod-receiving recess 206.

Figure 2A:
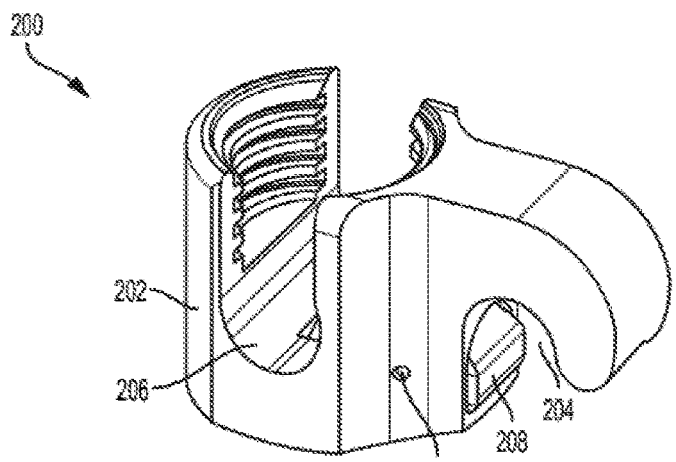
FIG. 2A is a perspective view of a prior art connector.
Figure 2B:
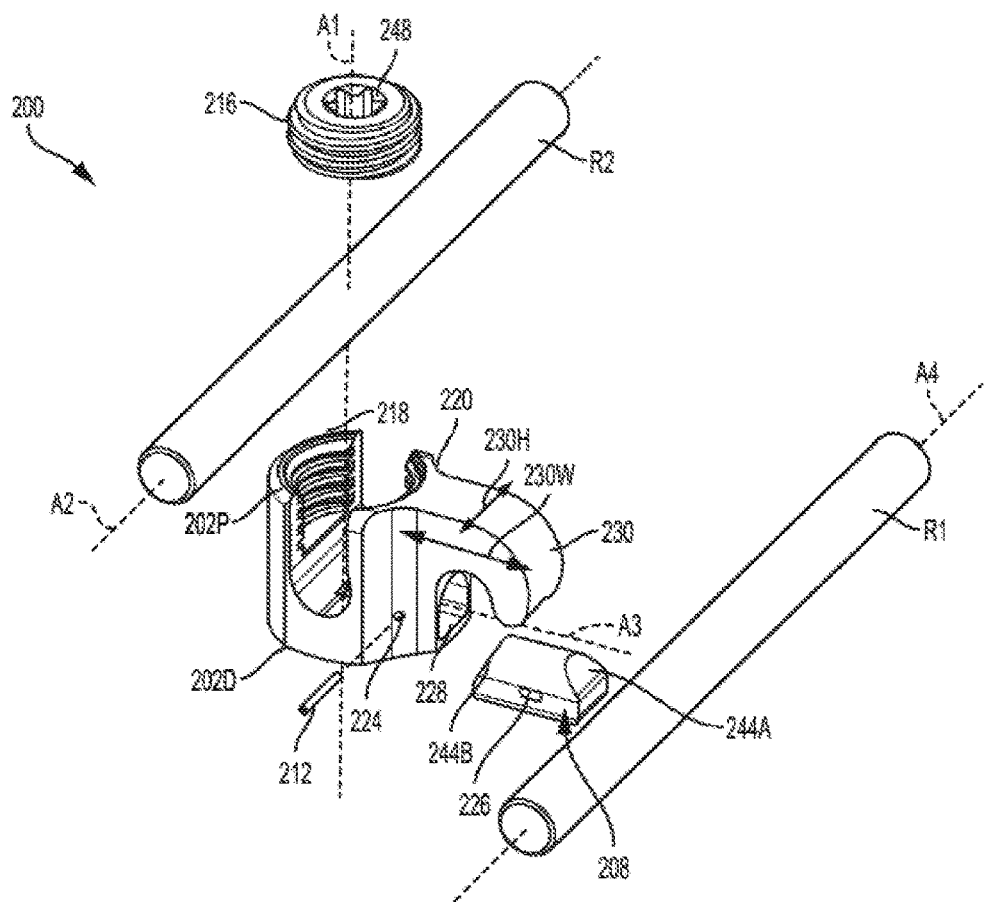
FIG. 2B is an exploded perspective view of the connector of FIG. 2A shown with first and second spinal rods.

The rod pusher 208 can include a through bore 226. The through-bore 226 can extend perpendicular or substantially perpendicular to the axis A3. The through-bore 226 can be sized to receive the spring wire 212 therein. In at least some positions of the rod pusher 208 with respect to the body 202, the through-bore 226 of the rod pusher can be aligned with the through-bore 224 of the body, such that the spring wire 212 extends through both through-bores 224, 226. As best shown in FIGS. 2D, 2F, and 2H, the through-bore 226 can include a middle portion and opposed end portions. The middle portion of the through-bore 226 can approximate the dimensions of the spring wire 212. For example, the middle portion can be cylindrical and can have a diameter that is substantially equal to the diameter of the spring wire 212. The end portions of the through-bore 226 can be elongated or can otherwise have a dimension greater than the diameter of the spring wire 212 to allow the rod pusher 208 to translate along the axis A3 and to accommodate the bend radius of the spring wire 212 during such translation.

The bias element can be configured to bias the rod pusher 208 towards the first rod-receiving recess 204. In the illustrated view, the bias element is a cylindrical spring wire 212.

The spring wire 212 can be formed from a resilient material such that, when deformed from a straight line, the spring wire tends to flex back towards its straight resting configuration. Accordingly, when deformed by movement of the rod pusher 208, the spring wire 212 can exert a force against the interior of the through-bore 226 to urge the rod pusher 208 towards the first rod-receiving recess 204. While a straight, cylindrical spring wire 212 is shown, various other bias elements can be used instead or in addition, such as non-straight or non-cylindrical wires, leaf springs, spring clips, wave springs, coil springs, and the like. The bias element can be omitted. For example, the rod pusher 208 can be free to float within the tunnel 228, or can be retained by a pin or other retention feature without being biased towards the first rod-receiving recess 204.

The set screw 216 can include an exterior thread configured to mate with the interior threads formed on the arms 218, 220 of the body 202 to allow the set screw to be advanced or retracted along the axis A1 with respect to the body by rotating the set screw about the axis A1. The set screw 216 can include a driving interface 248 configured to receive a driver for applying a rotational force to the set screw about the axis A1. The distal surface of the set screw 216 can be configured to contact and bear against a rod R2 disposed in the second rod-receiving 206 recess to lock the rod to the connector 200. When tightened against the rod R2, the set screw 216 can prevent the rod from translating relative to the connector 200 along the axis A2 and/or from rotating with respect to the connector about the axis A2. While a set screw 216 is shown, it will be appreciated that other locking elements can be used instead or addition, such as a closure cap that advances and locks by quarter-turn rotation, a closure cap that slides in laterally without rotating, a nut that threads onto an exterior of the connector 200, and so forth.

Operation of the connector 200 is illustrated schematically in FIGS. 2C-2H.

Figure 2C:
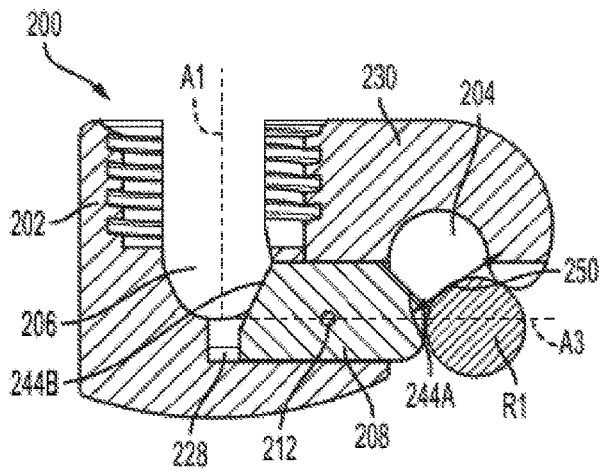
FIG. 2C is a sectional side view of the connector of FIG. 2A in a first configuration.
Figure 2D:
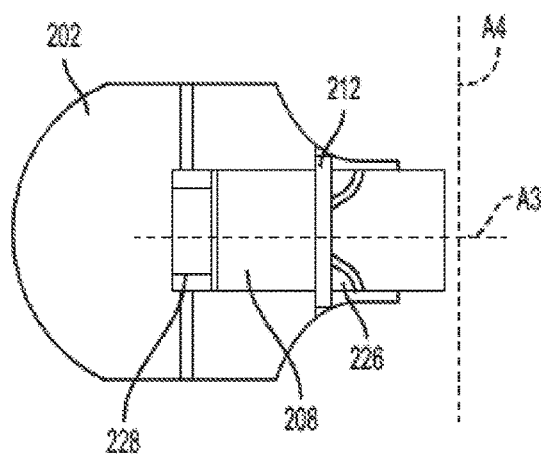
FIG. 2D is a sectional top view of the connector of FIG. 2A in the first configuration.

As shown in FIGS. 2C and 2D, the connector 200 can have a resting configuration in which no rod is disposed in the first or second rod-receiving recesses 204, 206. In this configuration, the biasing force of the spring wire 212 can cause the rod pusher 208 to slide towards the first rod-receiving recess 204.

Figure 2E:
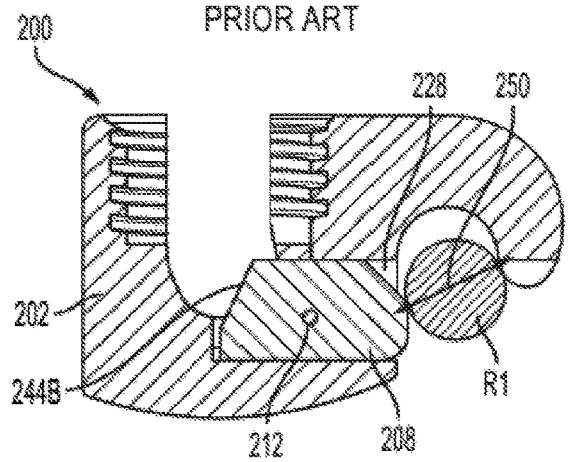
FIG. 2E is a sectional side view of the connector of FIG. 2A in a second configuration.
Figure 2F:
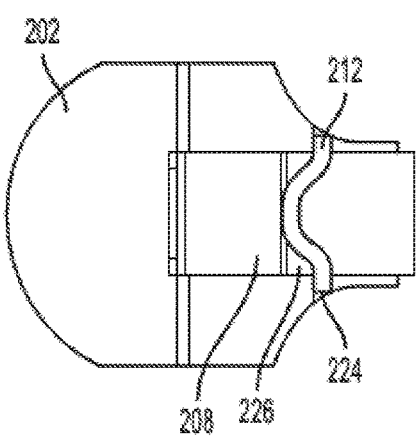
FIG. 2F is a sectional top view of the connector of FIG. 2A in the second configuration.

In the resting configuration, the wing portion 230 of the body 202 and the free end of the rod pusher 208 can define an aperture 250 that is smaller than the diameter of a first rod R1 to which the connector 200 is to be coupled. Accordingly, as shown in FIGS. 2E and 2F, as the rod R1 is inserted into the first rod-receiving recess 204, the rod bears against the rod pusher 208 to move the connector 200 out of the resting configuration. Insertion of the rod R1 can move the rod pusher 208 along the axis A3, thereby deforming the spring wire 212 from its resting state. As the largest cross-sectional portion of the rod R1 is positioned in the aperture 250, the rod pusher 208 can be displaced to its furthest distance from the first rod-receiving recess 204.

Figure 2G:
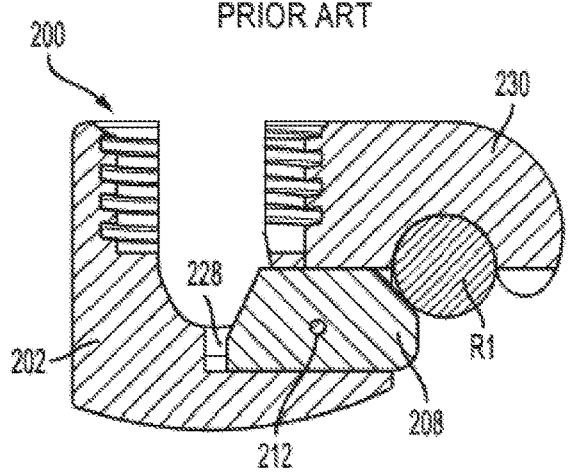
FIG. 2G is a sectional side view of the connector of FIG. 2A in a third configuration.
Figure 2H:
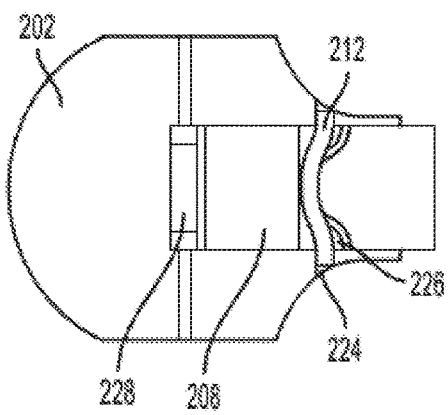
FIG. 2H is a sectional top view of the connector of FIG. 2A in the third configuration.
Figure 21:
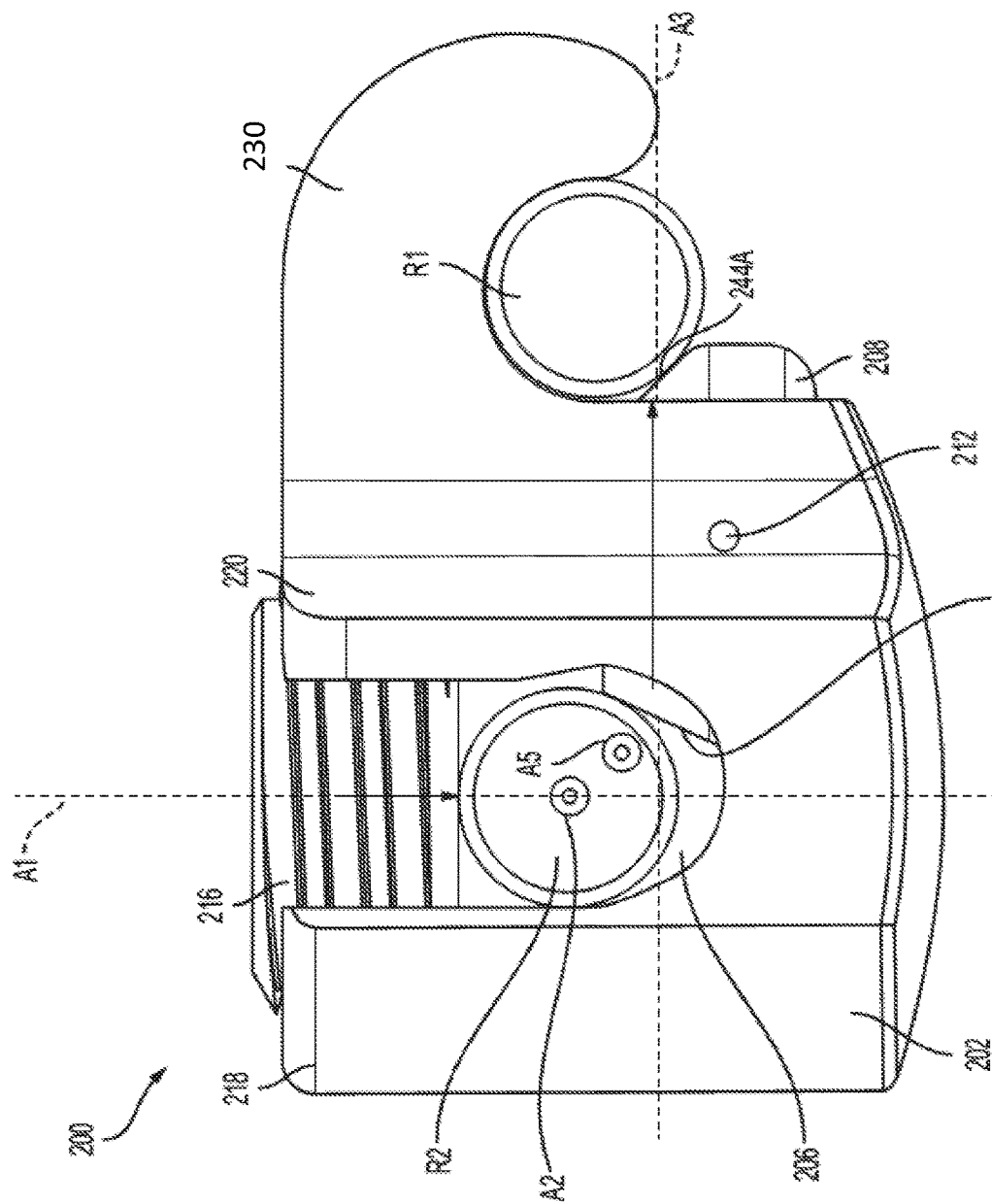

As shown in FIGS. 2G and 2H, once the largest cross-sectional portion of the rod R1 clears the aperture 250 as the rod is seated in the first rod-receiving recess 204, the biasing force of the spring wire 212 can cause the rod pusher 208 to move back along the axis A3 towards the first rod-receiving recess. This movement can at least partially close the aperture 250 around the rod R1 to capture the rod in the first rod-receiving recess 204. The biasing force of the spring wire 212 can resist retrograde movement of the rod pusher 208 and thus resist disconnection of the connector 200 from the first rod R1. The geometry of the connector 200 can be selected such that, when the rod R1 is fully seated in the first rod-receiving recess 204, the spring wire 212 is deformed from its resting state. The spring wire 212 can thus press the rod pusher 208 against the rod R1 to provide a friction or drag effect, before the set screw 216 is tightened and/or before a second rod R2 is positioned in the connector 200.

A second rod R2 can be positioned in the second rod-receiving recess 206, and the set screw 216 can be tightened to lock the connector 200 to the first and second rods R1, R2. As the set screw 216 is tightened, the second rod R2 can press against the second bearing surface 244B of the rod pusher 208, urging the rod pusher towards the first rod-receiving recess 204 and firmly into contact with the rod R1. When the set screw 216 is tightened, the connector 200 can be locked to the first and second rods R1, R2 to resist or prevent translation of the rods R1, R2 with respect to the connector along the axes A2, A4 and to resist or prevent rotation of the rods R1, R2 with respect to the connector about the axes A2, A4.

As shown in FIG. 2I, the second rod-receiving recess 206 can be shaped to encourage contact between the second rod R2 and the second bearing surface 244B of the rod pusher 208. In other words, the recess 206 can be shaped to reduce or eliminate the risk that the second rod R2 will only bear against the floor of the recess 206 when the set screw 216 is tightened, without applying sufficient force to the bearing surface 244B. As shown, the recess 206 can include a relief disposed in alignment with the end of the tunnel 228 such that the rod pusher 208 protrudes into the recess. The recess 206 can thus be asymmetrical about the axis A1, and can deviate from a symmetrical U-shape. When the rod R2 is bottomed out in the recess 206, the central longitudinal axis A2 of the rod can be offset from the axis A1. The central longitudinal axis of the rod R2 when the rod is fully seated is shown in FIG. 2I as axis A5. The recess 206 can be configured such that, as the rod R2 is seated within the recess 206, it translates distally along the axis A1 and laterally along the axis A3.

Figure 2J:
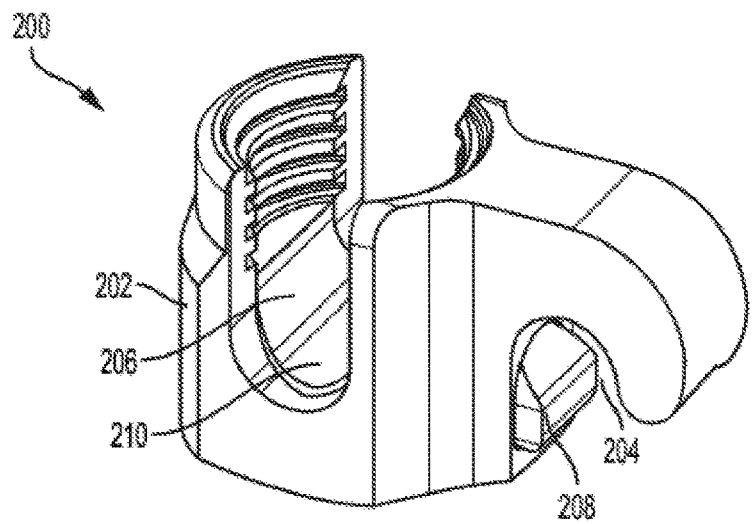
FIG. 2J is a perspective view of the connector of FIG. 2A shown with a saddle.
Figure 2K:
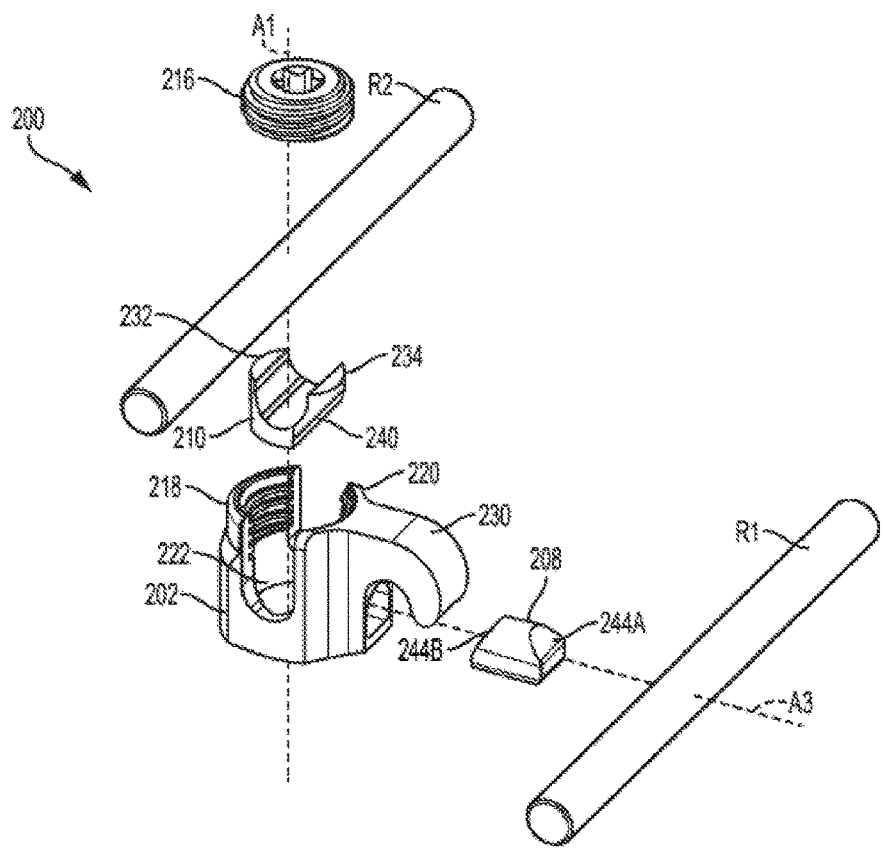
FIG. 2K is an exploded perspective view of the connector and saddle of FIG. 2J shown with first and second spinal rods.
Figure 2L:
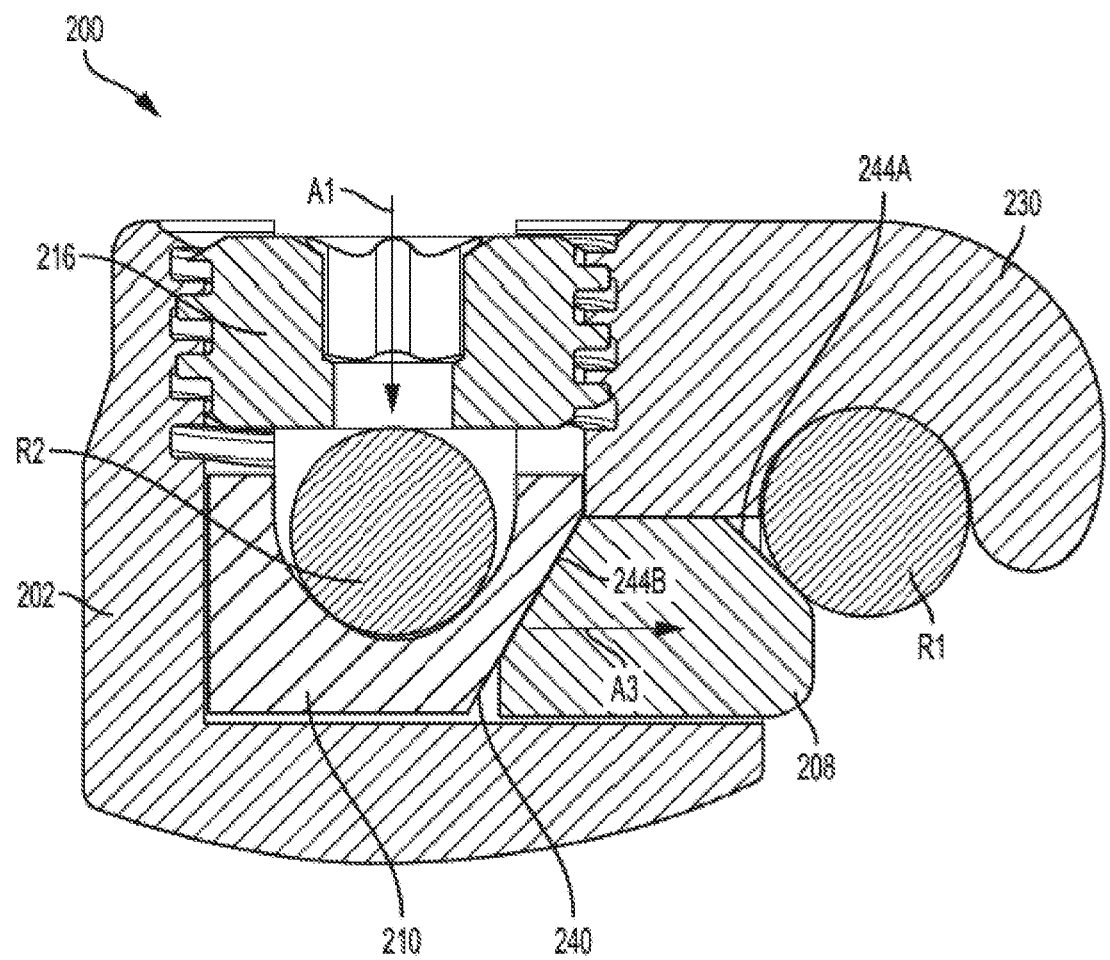
FIG. 2L is a sectional side view of the connector and saddle of FIG. 2J coupled to first and second spinal rods.

As shown in FIGS. 2J-2L, the connector 200 can include a saddle 210. The saddle 210 can be included in addition to the asymmetrical recess 206 or as an alternative thereto. The saddle 210 can be positioned within a cavity 222 formed in the body 202. The saddle 210 can be generally cylindrical with first and second arms 232, 234 extending in a proximal direction to respective free ends of the arms. The first and second arms 232, 234 can be aligned with the first and second arms 218, 220 of the body 202 such that a recess defined therebetween is aligned with the second rod-receiving recess 206. Accordingly, the second rod R2 can be simultaneously cradled between the arms 232, 234 of the saddle 210 and the arms 218, 220 of the body 202 when the rod is disposed in the second rod-receiving recess 206. The saddle 210 can include a ramped bearing surface 240 configured to contact and bear against the second bearing surface 244B of the rod pusher 208. The bearing surface 240 can extend at an oblique angle with respect to the axis A1. The bearing surface 240 can be planar as shown, or can be convex, concave, pointed, sharpened, etc. In operation, a force applied to the saddle 210 along the direction A1, e.g., by tightening the set screw 216 down onto the saddle or down onto a rod R2 disposed in the saddle, can cause the saddle 210 to translate distally with respect to the body 202 and cause the bearing surface 240 to ramp along the bearing surface 244B of the rod pusher 208, urging the rod pusher towards the first rod-receiving recess 204 along the axis A3. Accordingly, tightening the set screw 216 can be effective to simultaneously lock both rods R1, R2 to the connector 200.

The saddle 210 can allow for locking of rods having different diameters in the second rod-receiving recess 206, while still ensuring that, regardless of the diameter of the second rod R2, sufficient force is applied to the rod pusher 208 to lock the first rod R1.

Sometimes, the arms 232, 234 can extend proximally past the maximum dimension of the rod R2 and the set screw 216 can include an outer screw configured to bear against a proximal-facing surface of the arms. An inner set screw can be threadably mounted within the outer set screw. Accordingly, the outer set screw can be tightened first to press down on the saddle 210 and lock the first rod R1 in the first rod-receiving recess 204. Then, the inner set screw can be tightened to press down on the second rod R2 and lock the second rod in the second rod-receiving recess 206. The dual set screw can thus facilitate independent locking of the first and second rods R1, R2 to the connector 200. While not shown in FIGS. 2J-2L, connectors 200 that include a saddle 210 can also include a bias element as described above for biasing the rod pusher 208 towards the first rod-receiving recess 204.

The connector 200 can thus be used to connect a first spinal rod R1 to a second spinal rod R2. While use of the connector 200 with first and second spinal rods is generally described herein, it will be appreciated that the connector can instead be configured for use with other types of orthopedic hardware, whether implanted or external. For example, one or both halves of the connector 200 can be modified to couple other various components to each other (e.g., to couple a rod to a plate, to couple a plate to a plate, to couple a rod to cable, to couple a cable to a cable, and so forth).

The connector 200 can provide various benefits for the user and/or patient. For example, the biased rod pusher 208 can provide tactile feedback when the connector 200 is "snapped" onto the first rod R1, giving the user confidence that the rod has been attached successfully before tightening the connector. The biased rod pusher 208 can also apply friction or "drag" to the rod R1 prior to locking the set screw 216, helping to keep the connector in place and prevent "flopping" while still allowing free movement when intended by the user. By way of further example, the low-profile geometry of the wing portion 230 of the connector 200 can allow the connector to be used in surgical areas where space is limited (e.g., in the cervical area of the spine). In an exemplary method, the wing portion 230 of the connector 200 can be hooked onto a first rod R1 at a location between two bone anchors to which the rod is coupled, the two bone anchors being implanted in adjacent vertebral levels of the cervical spine. As yet another example, the connector 200 can facilitate simultaneous and/or single-step locking of the first and second rods R1, R2. This can allow the connector 200 to be locked to both rods R1, R2 with minimal steps. In other instances, the connector 200 can facilitate independent locking of the rods R1, R2, e.g., with use of a saddle 210 and dual set screw.

Exemplary connector and implants are disclosed in U.S. Patent Application Publication No. 2017/0333088, filed on Oct. 4, 2016, and in U.S. Patent Application Publication No. 2017/0333087, filed May 18, 2016, both of which are incorporated herein by reference.

Figure 3A:
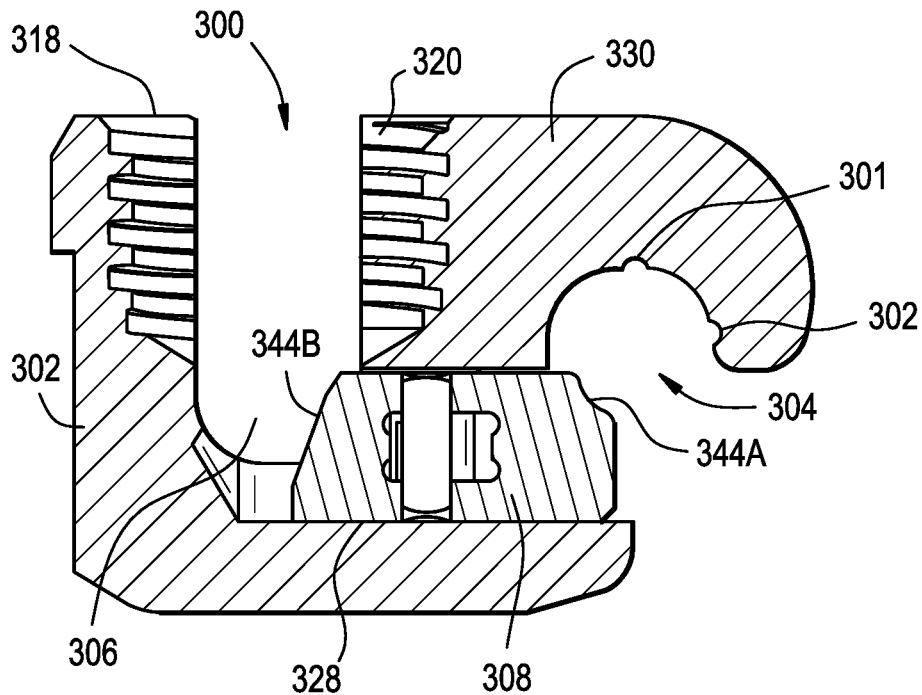
FIG. 3A is a cross-sectional view of one embodiment of a connector with a rod recess having two grip grooves.

FIG. 3A is a cross-sectional view of a connector with a rod recess having two grip grooves. As shown, the connector 300 can include a body 202 that defines first and second rod-receiving recesses 304, 306 and a rod pusher 308. The rod pusher 308 can be configured to translate laterally within the body 302, and can be biased in a direction that urges the rod pusher 308 into a first rod R1 disposed in the first rod-receiving recess 304. A set screw 216 can be tightened to lock the connector 300 to both the first rod R1 and to a second rod R2 disposed in the second rod-receiving recess 306. The illustrated connector 300 can thus allow for one-step locking of first and second rods R1, R2 to the connector (as shown in FIGS. 2A-2L). The connector 300 can include one or more low-profile portions to facilitate use in tight spaces. For example, the first rod-receiving recess 304 can be formed in a portion of the connector body 202 having a reduced-profile, e.g., to fit between bone anchors implanted in adjacent levels of the cervical spine.

The body 302 can include proximal and distal ends that define a proximal-distal axis A1, as shown in FIG. 2B. The proximal end of the body 202 can include a pair of spaced apart arms 318, 320 that define the second rod-receiving recess 306 therebetween. A rod R2 disposed in the second rod-receiving recess 306 can have a central longitudinal rod axis A2, as shown in FIG. 2B. The second rod-receiving recess 306 can be open in a proximal direction, such that a rod R2 can be inserted into the recess by moving the rod distally with respect to the connector 200. Each of the arms 318, 320 can extend from the distal portion of the body 302 to a free end. The outer surfaces of each of the arms 318, 320 can include a feature (not shown), such as a recess, dimple, notch, projection, or the like, to facilitate coupling of the connector 300 to various instruments. For example, the outer surface of each arm 318, 320 can include an arcuate groove at the respective free end of the arms for attaching the connector 300 to an extension tower or retractor. The arms 318, 320 can include or can be coupled to extension or reduction tabs (not shown) that extend proximally from the body 302 to functionally extend the length of the arms 218, 220. The extension tabs can facilitate insertion and reduction of a rod or other implant, as well as insertion and locking of the set screw 216, as shown in FIG. 2B. The extension tabs can be configured to break away or otherwise be separated from the arms 218, 220. The inner surfaces of each of the arms 318, 320 can be configured to mate with the set screw 216. For example, the inner surfaces of the arms 318, 320 can include threads that correspond to external threads formed on the set screw 316. Accordingly, rotation of the set screw 316 with respect to the body 302 about the axis A1 can be effective to translate the set screw with respect to the body axially along the axis A1.

The body 302 can include a cantilevered wing portion 330 that defines the first rod-receiving recess 304. As shown in FIG. 2B, a rod R1 disposed in the first rod-receiving recess 304 can have a central longitudinal rod axis A4. The axis A4 can be parallel to the axis A2 as shown, or can be perpendicular or obliquely angled with respect to the axis A2. The wing portion 330 can extend radially-outward from the second arm 320 of the body 302. The first rod-receiving recess 304 can be open in a distal direction such that a rod R1 can be inserted into the recess by moving the connector 300 distally with respect to the rod. The first rod-receiving recess 304 can be open in a proximal direction, e.g., by flipping the wing portion 330 and forming it such that it extends from a distal portion of the body 302, or in a lateral direction.

The rod pusher 308 can be slidably disposed within the tunnel 328 of the body 302 and can be configured to translate with respect to the body along the axis A3, as shown in FIG. 2B. The rod pusher 308 can include a first bearing surface 344A configured to contact and bear against a first rod R1 disposed in the first rod-receiving recess 304. The bearing surface 344A can extend at an oblique angle with respect to a longitudinal axis of the rod pusher 308 such that the bearing surface is ramped. The bearing surface 344A can be planar as shown, or can be convex, concave, pointed, sharpened, etc. For example, the bearing surface 344A can be concave and can define a section of a cylinder, such that the bearing surface matches or approximates the contour of a cylindrical rod R1 disposed in the first rod-receiving recess 204. The rod pusher 308 can include a second bearing surface 344B configured to contact and bear against a second rod R2 disposed in the second rod-receiving recess 306. The bearing surface 344B can extend at an oblique angle with respect to a longitudinal axis of the rod pusher 208 such that the bearing surface is ramped. The bearing surface 344B can be planar as shown, or can be convex, concave, pointed, sharpened, etc. For example, the bearing surface 344B can be concave and can define a section of a cylinder, such that the bearing surface matches or approximates the contour of a cylindrical rod R2 disposed in the second rod-receiving recess 306.

FIG. 3A shows the first rod-receiving recess 304 including two grip grooves 301 opposite to the bearing surface 344A. The grip grooves 301 are formed as recesses in the inner surface of the first rod-receiving recess 304, as shown more clearly in FIG. 3B.

Figure 3B:
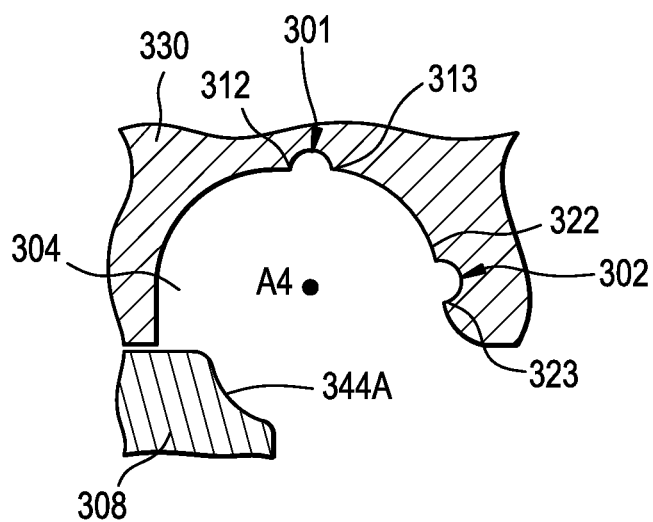
FIG. 3B is a cross-sectional view of the rod-receiving recess of the connector of FIG. 3A.

FIG. 3B is a cross-sectional view of the rod-receiving recess 304 of the connector of FIG. 3A. FIG. 3B shows that the grip grooves 301 each define two edges 312, 313, 322, 323 that are configured to contact the surface of the cylindrical rod R1 disposed in the first rod-receiving recess 304. The grip grooves 301 extend along the axis A4 and the first rod-receiving recess 304 is sized and shaped such that the side of the cylindrical rod R1 that faces the grip grooves 301 is urged into contact against the edges 312, 313, 322, 323 by the rod pusher 308, such that additional force applied to the cylindrical rod R1 by the rod pusher 308 further engages the cylindrical rod R1 against the edges 312, 313, 322, 323. This can be accomplished by, for example, having the inner surface of the rod-receiving recess 304 and the location of the grip grooves 301 sized and shaped such that the edges 312, 313, 322, 323 define a radius about the axis A4 that approximately matches the radius of the cylindrical rod R1 and, when the cylindrical rod R1 is urged into the rod-receiving recess 304, the half of the cylindrical rod R1 opposite the first bearing surface 344A of the rod pusher contacts the rod-receiving recess 304 only at engages the edges 312, 313, as shown in more detail in FIG. 3C.

Figure 3C:
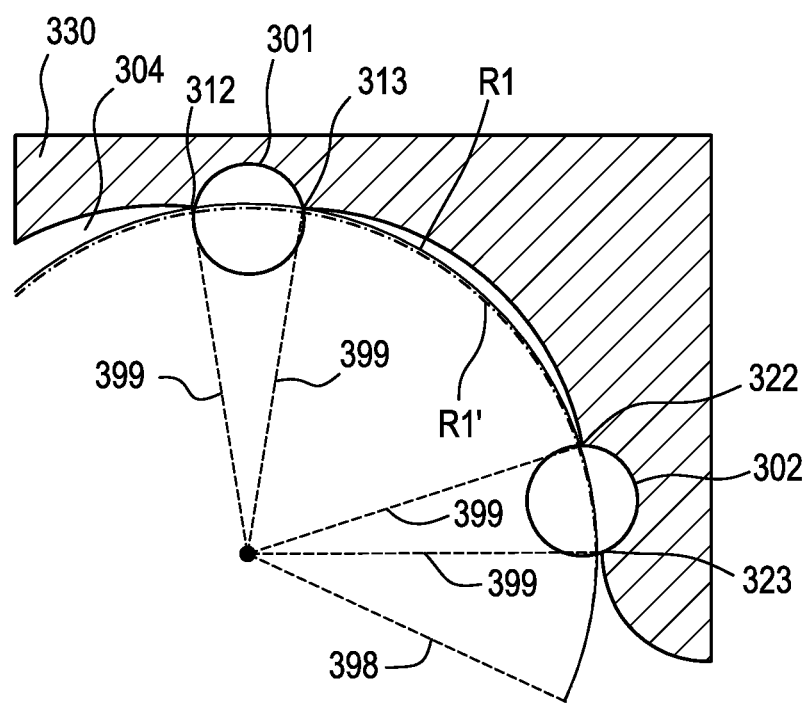
FIG. 3C is a cross-sectional view of the grip grooves of the rod-receiving recess of the connector of FIG. 3A.

FIG. 3C is a cross-sectional view of the grip grooves 301 of the rod-receiving recess 304 of the connector 300 of FIG. 3A. FIG. 3C shows the cylindrical rod R1 (solid line) disposed in the rod-receiving recess 304 and in contact with the edges 312, 313, such that a small portion of the outer surface of the cylindrical rod R1 is received inside each grip groove 301. This illustrated configuration shows that the cylindrical rod R1 makes contact with the rod-receiving recess 304 along 4 points of contact, in contrast with the prior art rod-receiving recess 204 without grip grooves. This prior art configuration is shown in FIG. 3C as the position of a cylindrical rod R1' is overlaid the cylindrical rod R1. The position of a cylindrical rod R1' (dotted line) corresponds to position the cylindrical rod R1' in the rod-receiving recess 304 without grip grooves 301 as shown more clearly in FIG. 4A. FIG. 3C shows the radius 398 of the cylindrical rod R1 and the distance 399 of each edge 312, 313 from the central longitudinal axis A4 of the rod-receiving recess 304 are approximately the same.

Figure 4A:
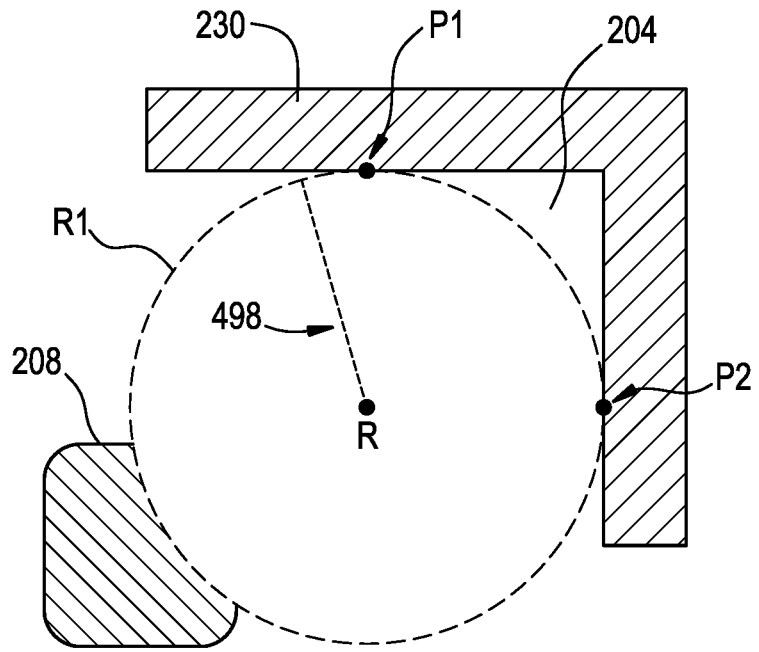
FIG. 4A is a cross-sectional view of a prior art rod-receiving recess.

FIG. 4A is a cross-sectional view of a prior art rod-receiving recess. FIG. 4A shows a cylindrical rod R1 disposed in a prior art rod-receiving recess 204 without grip grooves. In this configuration, the cylindrical rod R1 contacts the inner surface of the rod-receiving recess 204 at two points P1, P2. In operation, these two points P1, P2 can define parallel lines of contact along the axis A4 (e.g., along the surface of the cylindrical rod R1 that contacts the inner surface of the rod-receiving recess 204). The particular interface of the cylindrical rod R1 and the rod-receiving recess 204 at these points P1, P2 is a curved surface (e.g., the cylindrical rod R1) against a flat or angled surface (e.g., the rod-receiving recess 204). With this engagement, both the rotation of the cylindrical rod R1 about axis A4 and translation of the cylindrical rod R1 in the A4 direction are restrained by the force applied by surface of the rod-receiving recess 204 against the cylindrical rod R1, which depends on the force applied by the rod pusher 208 and the friction forces between the cylindrical rod R1 and the surface of the rod-receiving recess 204. The radius 498 of the cylindrical rod R1 is shown with respect to the central axis R of the cylindrical rod R1.

Figure 4B:
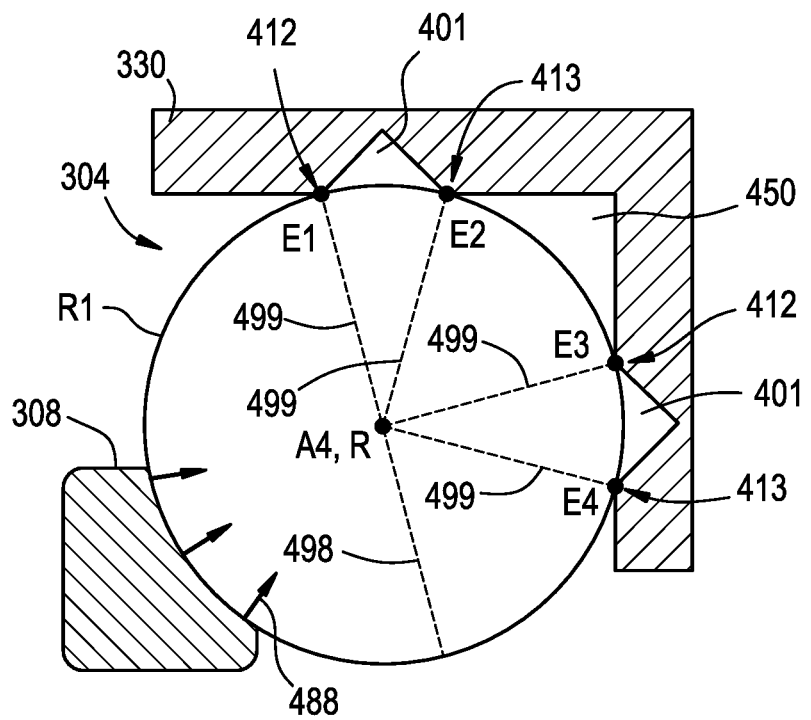
FIG. 4B is a cross-sectional view of one embodiment of a rod-receiving recess having v-shaped grip grooves.

As illustrated in FIG. 4B, aspects of the present disclosure provide improved retaining of the cylindrical rod R1 in a rod-receiving recess 304. FIG. 4B is a cross-sectional view of a rod-receiving recess 308 having v-shaped grip grooves 401. The-shaped grip grooves 401 define edges 412, 413 that are positioned to be contacted by the surface of the cylindrical rod R1 at points E1-E4. That is, the v-shaped grip grooves 401 are formed in the surface of the rod-receiving recess 304 such that the edges 412, 413 define four points on a circle with a radius approximately the same as the cylindrical rod R1. In operation, the cylindrical rod R1 rests against the four edges 412, 413 and rod pusher 308 applies a force 488 to the cylindrical rod R1 that urges the surface of the cylindrical rod R1 against the edges 412, 413. In contrast to the prior art surface-to-surface engagement of FIG. 4A, the curved surface of the cylindrical rod R1 is pressed against sharp edges 412, 413 (e.g., corners or apexes creating an edge of a sufficiently small radius or thickness to be able to be deformed by the cylindrical rod R1 or to deform the surface of the cylindrical rod R1 to allow the cylindrical rod R1 to be urged into the grip grooves 401), such that rotation of the cylindrical rod R1 while pressed against the four edges 412, 413 requires micro shearing of the edges 412, 413 at the points of contact E1-E4. Accordingly, the grip grooves 401 constrain the rotation of the cylindrical rod R1 in the rod-receiving recess 304 in a manner that requires material property failure to allow movement between the edges 412, 413 and the cylindrical rod R1. As a result, for an equal force applied to the cylindrical rod R1 by the rod pusher 308, the grip grooves 401 are able to withstand higher torque on the cylindrical rod R1 about axis A4 before movement occurs.

In some instances, in order to ensure the engagement between the cylindrical rod R1 and the edges 412, 413, a pocket 450 is formed in the rod receiving recess 304, such that the movement of the cylindrical rod R1 against the edges 412, 413 as driven by the rod pusher 308 is not interrupted by the cylindrical rod R1 contacting the inner surface of the rod receiving recess 308. This configuration can allow the initial urging of the cylindrical rod R1 against the edges 412, 413 to create some deformation at the points of contact E1-E4 (e.g., deformation of either of the material of the cylindrical rod R1, the edges 412, 413, or both), such that any initial rotation of the cylindrical rod R1 induces further material deformation at the points of contact E1-E4.

While FIG. 4B shows the body 302 having two grip grooves 401, in some instances, the body 302 has only one grip groove 401, for example, with the single grip groove 401 located opposite the clamping force vector, such that the force vector 488 and the center of the grip groove 401 intersects the central axis A4 of the rod R1.

FIG. 4B also shows the radius 498 of the cylindrical rod R1 and the distance 499 of each edge 412, 413 from the central longitudinal axis A4 of the rod-receiving recess 304 can be approximately the same to allow the surface of the cylindrical rod R1 to evenly contact the edges 412, 413, in which case the central axis R of the cylindrical rod R1 is concentric with the central longitudinal axis A4 of the rod-receiving recess 304.

Figure 4C:
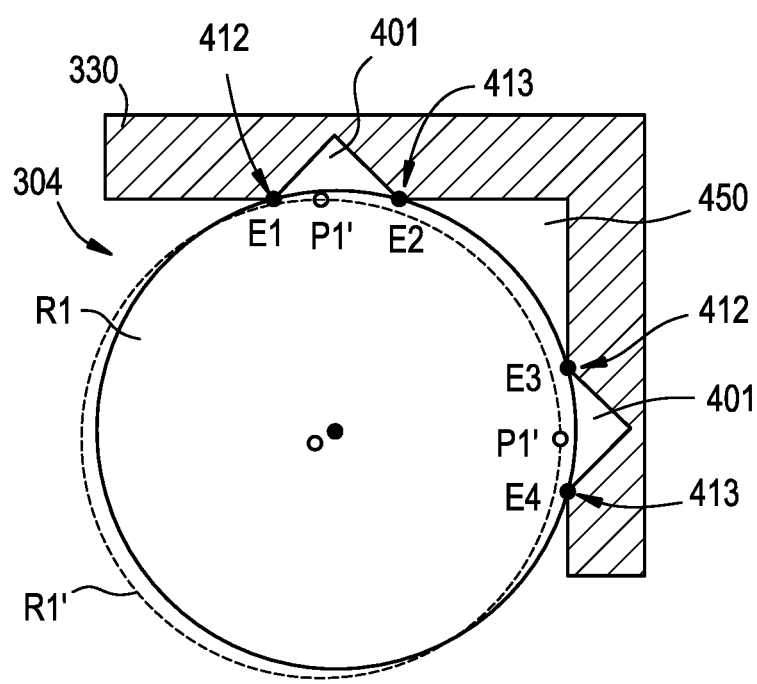
FIG. 4C is a cross-sectional view of the rod-receiving recess of FIG. 4B showing a comparison of the position of a rod with and without the grip grooves.

FIG. 4C is a cross-sectional view of the rod-receiving recess 304 of FIG. 4B showing a comparison of the position of a cylindrical rod R1 with and without the grip grooves 401. FIG. 4C shows both the position of cylindrical rod R1 engaged with the grip grooves 401 as shown in FIG. 4B, as well as the same cylindrical rod R1 positioned in the rod-receiving recess 204 without the grip grooves 401 (as shown by dotted line R1'). Compared with the position of the cylindrical rod R1' against the rod-receiving recess 204, the cylindrical rod R1 in the rod-receiving recess 304 having the grip grooves 401 is positioned farther into the pocket 450 because a small portion of the surface of the cylindrical rod R1 is received into the grip grooves 401 to allow the edges 412, 413 to all contact the surface of the cylindrical rod R1.

Figure 4D:
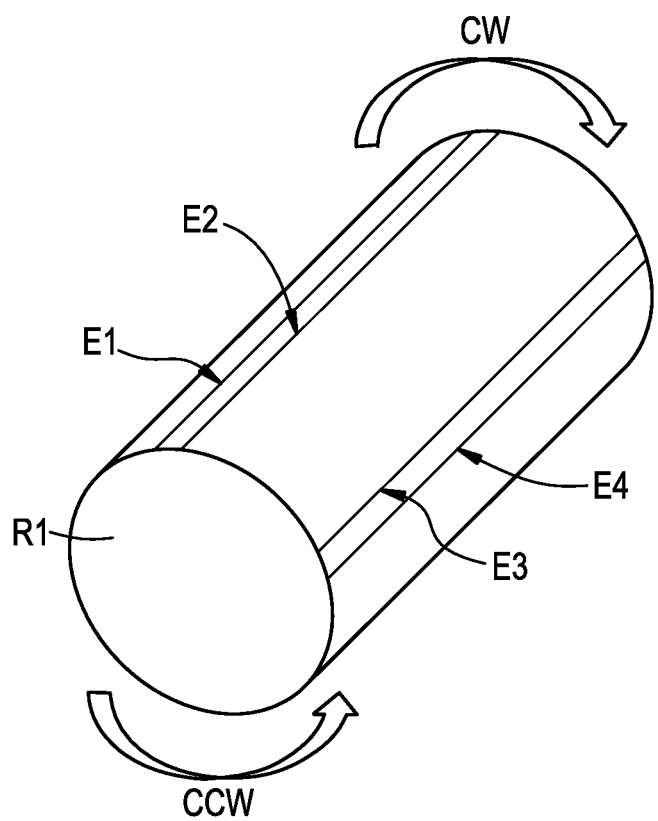
FIG. 4D is a perspective view of a rod showing lines of contact made by the edges of the two grip grooves of FIG. 4B when the rod is positioned in the rod-receiving recess of FIG. 4B.

FIG. 4D is a perspective view of a cylindrical rod R1 showing lines of contact E1-E4 made by the edges 412, 413 of the two grip grooves 401 when the cylindrical rod R1 is positioned in a rod-receiving recess 304 (as shown in FIG. 4B). FIG. 4D shows the resultant contact between a rod-receiving recess 304 with grip grooves 401 that span the length of the cylindrical rod R1. This allows the cylindrical rod R1 to be pressed into the edges 412, 413 along the lines of contact E1-E4 such that the force applied to the cylindrical rod R1 is not disrupted by contact between the cylindrical rod R1 and the rod-receiving recess 304 except for along the lines of contact E1-E4. In some instances, and as explained in more detail below, additional points and lines of contact between the cylindrical rod R1 and the rod-receiving recess 304 are within the scope of this disclosure, however, such additional contacts still permit a sufficient portion of the force applied to cylindrical rod R1 to be directed against the edges 412, 413 along the lines of contact E1-E4 in order to create the condition whereby rotation of the cylindrical rod R1 is resisted by a requirement for material deformation of one or both of the cylindrical rod R1 and the edges 412, 413 along the lines of contact E1-E4. FIG. 4D shows that the lines of contact E1-E4 are oriented to resist rotation of the cylindrical rod R1 in both the clockwise CW and counterclockwise CCW directions.

Figure 4E:
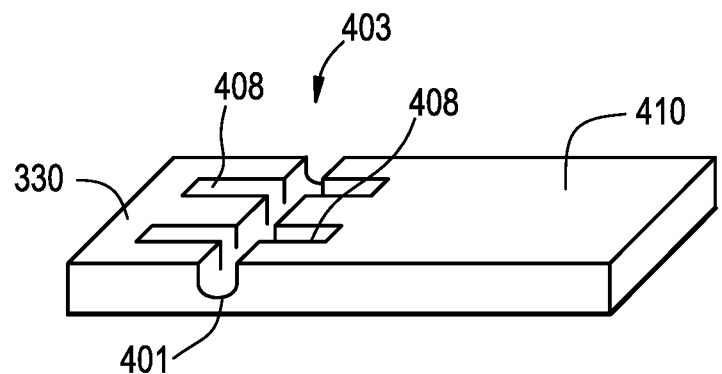
FIG. 4E is a perspective view of a surface of one embodiment of a rod-receiving recess with a segmented grip groove.

FIG. 4E is a perspective view of a surface 410 of a rod-receiving recess 304 with a segmented grip groove 403. The segmented grip groove 403 is formed when a grip groove 401 is intersected by one or more recesses or grooves 408. FIG. 4E shows the segmented grip groove 403 formed by a grip groove 401 that is intersected by two recesses 408 oriented at right angles to the grip groove 401. In some embodiments, however, other angles are possible such that the one or more recesses or grooves 408 are transverse to the grip groove 401 (e.g., oblique to, etc.). The intersection of the grip groove 401 by the grooves 408 creates breaks in the grip groove edges 412, 413 along the length of the cylindrical rod R1, as shown in FIG. 4F, which are now referred to as segmented edges 412, 413.

Figure 4F:
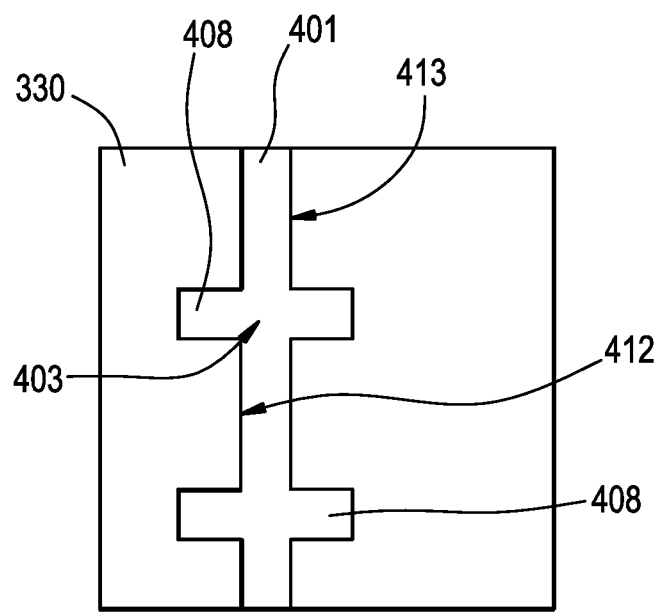
FIG. 4F is a top-down view of the segmented grip groove of FIG. 4E.
Figure 4G:
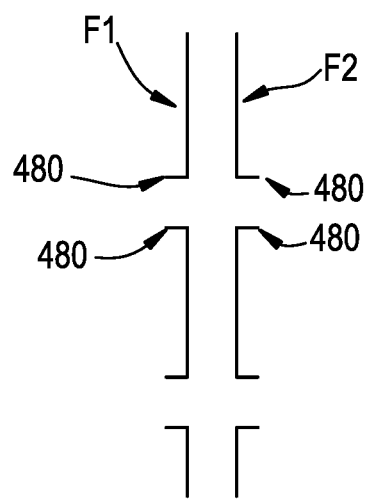
FIG. 4G is an schematic illustration of the contact points on a rod engaged with the segmented grip groove of FIG. 4E.

FIG. 4F is a top-down view of the segmented grip groove of FIG. 4E. In operation, the segmented edges 412, 413 serve to constrain movement of the cylindrical rod R1 along the length of the segmented grip groove 403 (i.e., translation along axis A4) by creating point edges 480 (e.g., small corners as the rod is urged into the groove and each point edge 480 forms a small corner of contact with the rod R1), as shown in FIG. 4G that engage the surface of the cylindrical rod R1 and enable the segmented edges 412, 413 to apply a force on the cylindrical rod R1 in the A4 direction. FIG. 4G is a schematic illustration of the contact points F1-F4 on the cylindrical rod R1 engaged with the segmented grip groove 403 of FIG. 4E. FIG. 4G shows that when the cylindrical rod R1 is pressed into engagement with the segmented grip groove 403, the resulting contact lines F1, F2 of the segmented edges 412, 413 are segmented as well. With the cylindrical rod R1 engaged with the segmented edges 412, 413, the point edges or small corners 480 define the transition between a point on the cylindrical rod R1 where the segmented edges 412, 413 are and are not contacting the cylindrical rod R1. If, for example, the material properties of the cylindrical rod R1 and the segmented edges 412, 413 are chosen such that the surface of the cylindrical rod R1 is deformed when in contact with the segmented edges 412, 413, then the point edges 480 together resist translation of the rod along the segmented grip groove 403 (i.e., translation along axis A4) by virtue of this movement resulting in two of the four illustrated point edges 480 being driven into an un-deformed region of the surface of the cylindrical rod R1. Therefore, the segmented grip groove 403 can resist both rotation and translation of the cylindrical rod R1 in the rod-receiving recess 403, as shown in FIG. 4F.

Figure 4H:
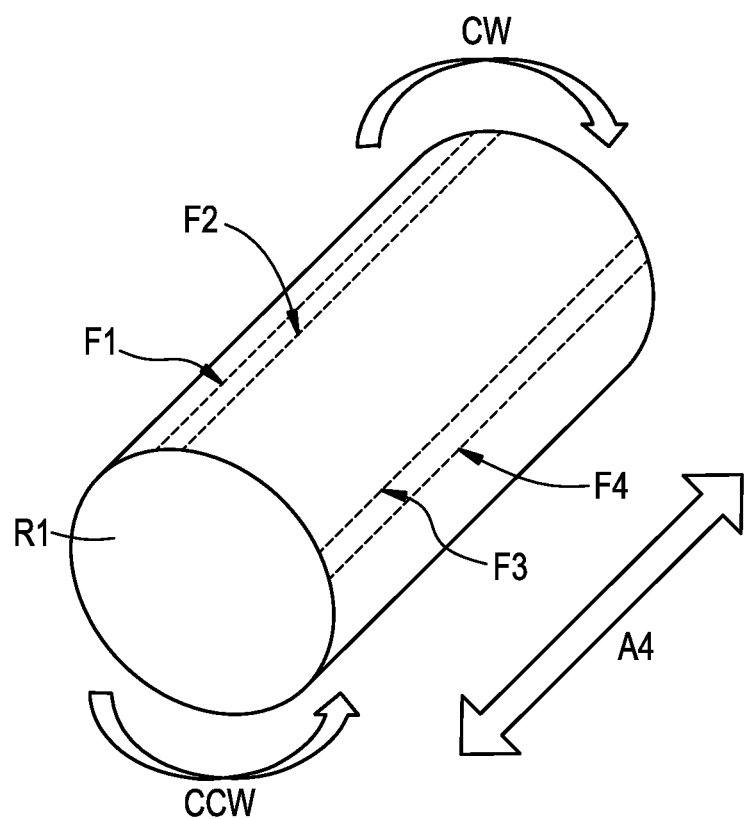
FIG. 4H is a perspective of a surface of a rod showing lines of contact made by the edges of the two segmented grip grooves of FIG. 4E when the rod is positioned in the rod-receiving recess of FIG. 4E.

FIG. 4H is a perspective of a surface of a cylindrical rod R1 showing segmented lines of contact F1-F4 made by the edges of two segmented grip grooves 403 when the cylindrical rod R1 is positioned in the rod-receiving recess 304. Clockwise CW and counterclockwise CCW rotation of the cylindrical rod R1 is resisted by the segmented grip grooves 403 in the same manner as described above with respect to non-segmented grip grooves 401, and translation of the cylindrical rod R1 is resisted by the point edges 480 created between the segmented edges 412, 413

Figure 5A:
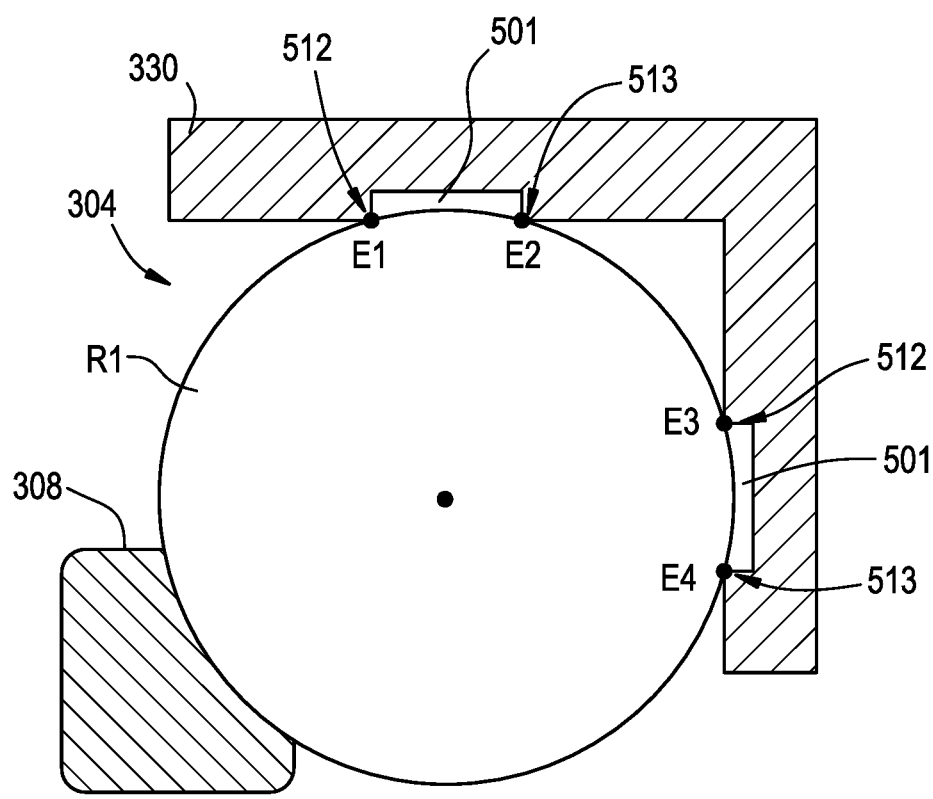
FIG. 5A is a cross-sectional view of one embodiment of a rod-receiving recess having grip grooves of an alternative shape.
Figure 5B:
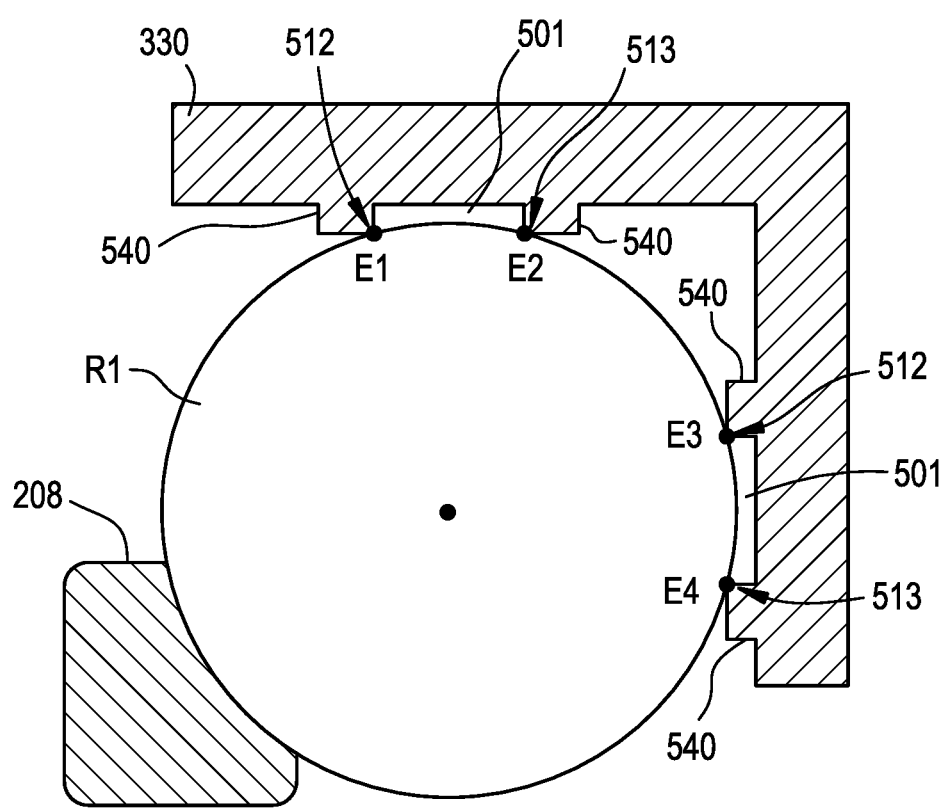
FIG. 5B is a cross-sectional view of one embodiment of a rod-receiving recess having grip grooves formed by protrusions.

While FIG. 3A shows grip grooves 301 having a cylindrical shape and FIG. 4B shows grip grooves 401 having a V-shape, other shapes are possible. For example, FIG. 5A is a cross-sectional view of a rod-receiving recess 403 having grip grooves 501 of a rectangular shape, where the edges 512, 513 are right angles. FIGS. 3A-5A show the grip grooves 301, 401, 501 as recesses formed on the inner surface of the rod-receiving recess 304, but the grip grooves can also be formed by protrusions 540 extending from the inner surface of the rod-receiving recess 304, as shown in FIG. 5B.

Figure 6A:
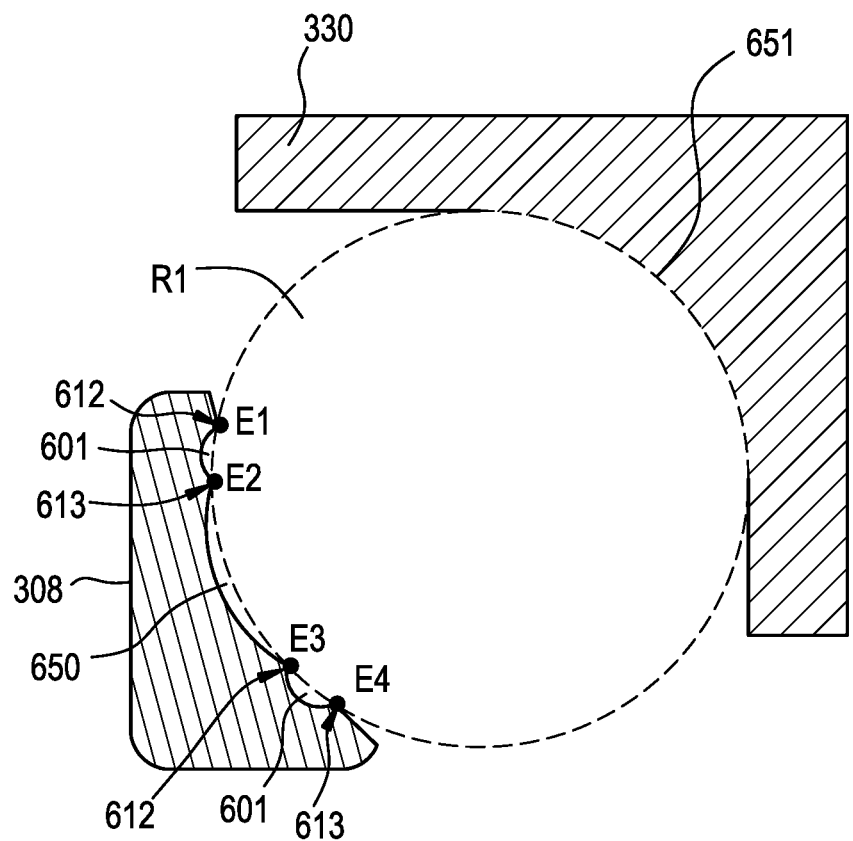
FIG. 6A is a cross-sectional view of one embodiment of a rod-receiving recess and a rod pusher having grip grooves.
Figure 6B:
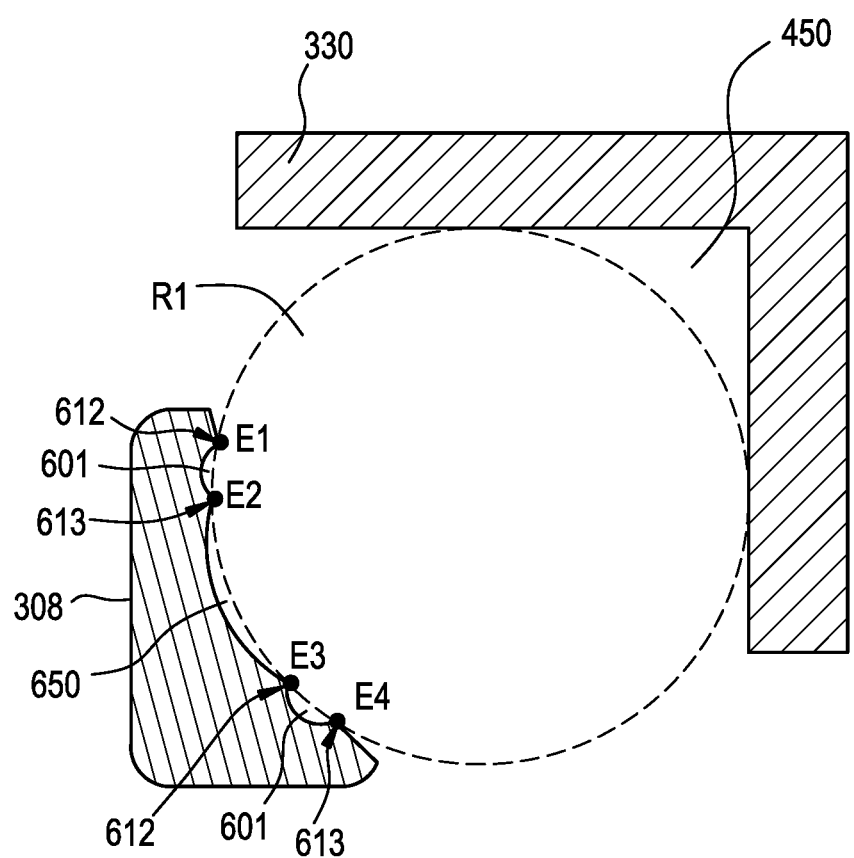
FIG. 6B is a cross-sectional view of an alternate embodiment of a rod-receiving recess and with a rod pusher having grip grooves.
Figure 6C:
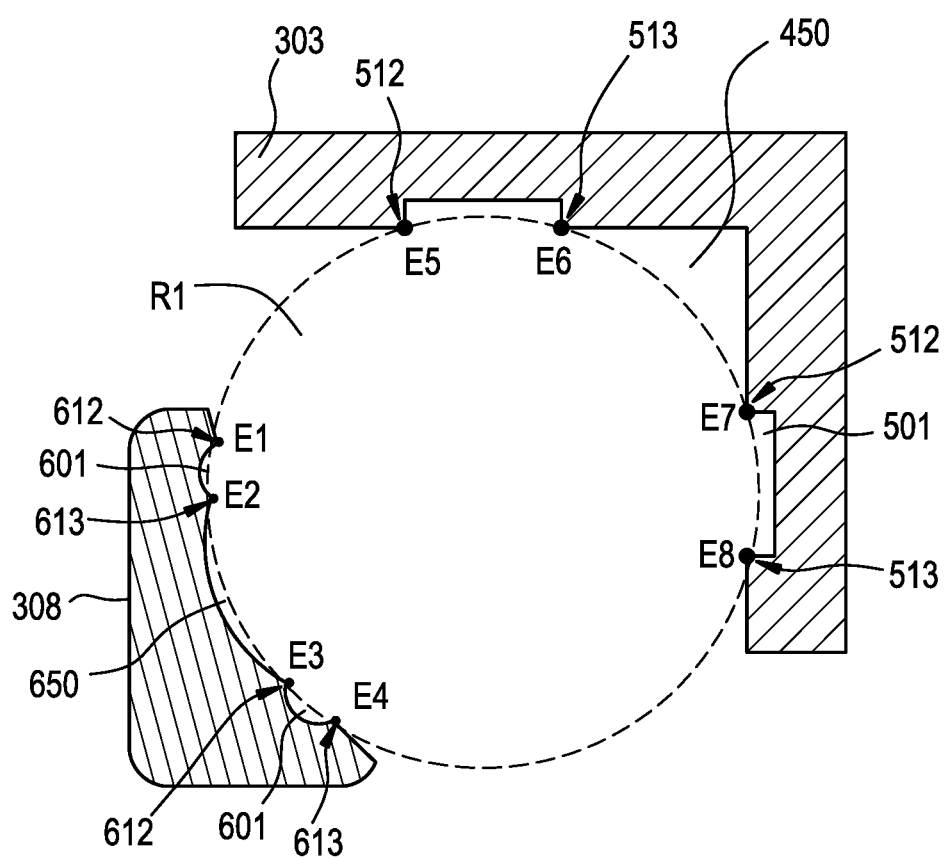
FIG. 6C is a cross-sectional view of one embodiment of a rod-receiving recess and rod pusher both having grip grooves.

FIGS. 3A-5B show the grip grooves 301, 401, 501 formed on wing portion 330 of the body 302 with the rod pusher 308 arranged to apply a force to the cylindrical rod R1 to drive the cylindrical rod R1 against the grip grooves 301, 401, 501, but other configurations are possible. For example, FIG. 6A is a cross-sectional view of a rod-receiving recess 304 with the rod pusher 308 having grip grooves 601. As shown, the grip grooves 601 define edges 612, 613 that contact the cylindrical rod R1 at four contact points E1-E4 that define a circle of approximately the same radius as the cylindrical rod R1. In FIG. 6A, the surface of the rod-receiving recess opposite the rod pusher 308 defines a curved surface 651 that contacts the cylindrical rod R1 to apply a force that opposes the force applied to the cylindrical rod R1 by the edges 612, 613 of the grip grooves 601 of rod pusher 308. In operation, the grip grooves 601 of the rod pusher 308 function in the same manner as the grip grooves 301, 401, 501 described above. FIG. 6B is a cross-sectional view of a rod-receiving recess 304 with a pocket 450 and a rod pusher 308 having grip grooves 601. FIG. 6C shows both the rod-receiving recess 304, grip grooves 501, and the rod pusher 308 having grip grooves 601. In this configuration, the position of the cylindrical rod R1 is highly constrained by the grip grooves 501, 601 as the eight points of contact E1-E8 all engage with the surface of the cylindrical rod R1. However, in some instances, the tolerances in the positions of the eight points of contact E1-E8 is reduced upon initial contact with the cylindrical rod R1 such that the cylindrical rod R1 is highly constrained once sufficient force is applied to sufficiently engage the cylindrical rod R1 about the eight points of contact E1-E8.

Figure 7A:
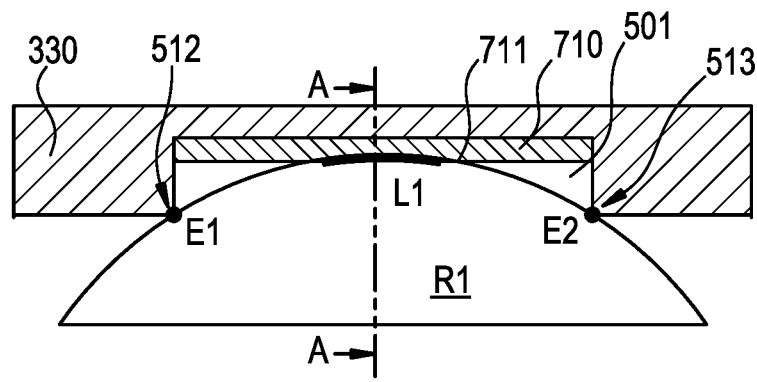
FIG. 7A is a cross-sectional view of one embodiment of a single grip groove having an internal protrusion arranged to contact the rod in the grip groove perpendicular to the edges of the grip groove.

FIG. 7A is a cross-sectional view of a single grip groove 501 having an internal protrusion 710 arranged to contact the surface of the cylindrical rod R1 between the edges 512, 513 of the grip groove 501. In order to increase the restraint of the cylindrical rod R1 in the translational direction (i.e., along axis A4), additional grip features can be included inside the grip groove 501 in order to provide translational restraint with a minimal to negligible effect on the rotational restraint provided by the edges 512, 513. In FIG. 7A the grip groove 501 includes one or more protrusions 701 along the length of the grip groove 501. The internal protrusions 710 extend towards the cylindrical rod R1 and include a feature, such as end edge 711 that is positioned to contact the cylindrical rod R1 when the cylindrical rod R1 is engaged with the edges 512, 513 of the grip groove 501. FIG. 7A shows an internal protrusion 710 with an edge 711 contacting the cylindrical rod R1 along a line of contact L1 that is perpendicular to the lines of contact E1, E1 created by the edges 512, 513. In operation, the position and shape of the edge 711 in the grip groove 501 can be configured to vary the strength of the contact line L1 between the cylindrical rod R1 and the edge 711 when the cylindrical rod R1 is in contact with the edges 512, 513, as shown in more detail in FIGS. 7D and 7E.

Figure 7B:
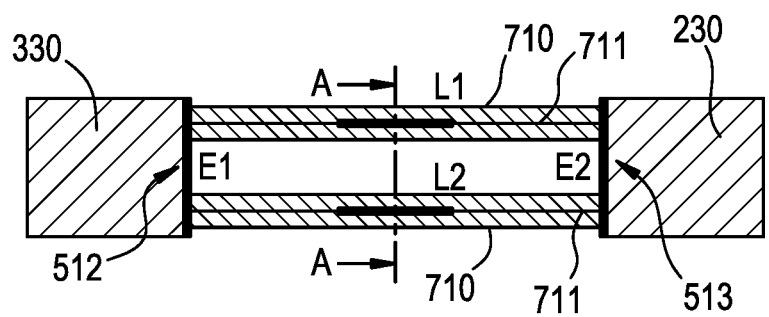
FIG. 7B is a top-down view of the grip groove of FIG. 7A showing the perpendicular edges of the internal protrusion.
Figure 7C:
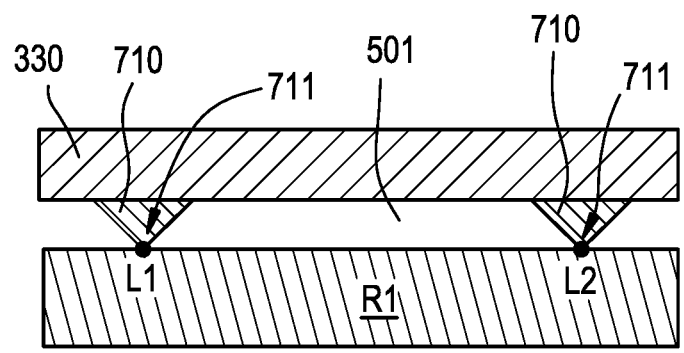
FIG. 7C is a cross-sectional view of the grip groove of FIG. 7A showing the edges of the internal protrusions contacting the rod when the rod is engaged with the grip groove.

FIG. 7B is a top-down view of the grip groove 501 of FIG. 7A showing the perpendicular edges 711 of two internal protrusions 710 creating two parallel lines of contact L1, L2 on the cylindrical rod R1. FIG. 7C is a cross-sectional view of the grip groove 501 of FIG. 7A showing the edges 711 of the internal protrusions 710 contacting the cylindrical rod R1 when the rod is engaged with the grip groove 501.

Figure 7D:
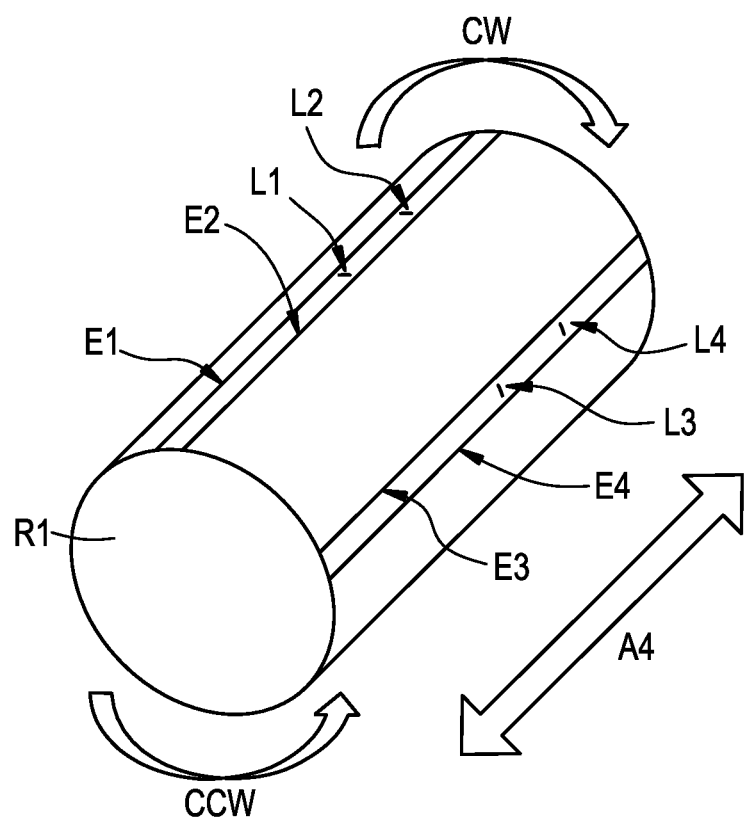
FIG. 7D is a perspective view of a rod showing lines of contact made by the edges of the two grip grooves of FIG. 7A with internal protrusions.

FIG. 7D is a perspective view of a cylindrical rod R1 showing lines of contact E1-E4 made by the edges 512, 513 of two grip grooves 501 and the lines of contact L1-L4 made by two internal protrusions 710 in each grip groove 501. In operation, the lines of contact E1-E4 made by the edges 512, 513 resist rotation of the cylindrical rod R1 in the clockwise CW and counterclockwise CCW directions, and the lines of contact L1-L4 made by two internal protrusions 710 resist translation of the cylindrical rod R1 in the A4 direction.

Figure 7E:
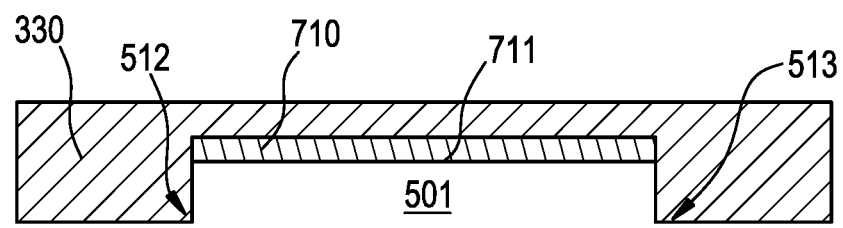
FIGS. 7E and 7F are cross-sectional views of embodiments of a single grip groove having an internal protrusion with two different configurations.
Figure 7F:
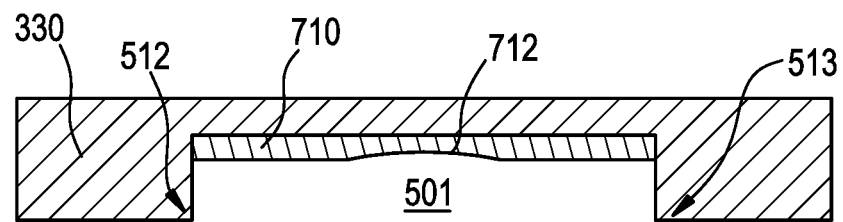

FIGS. 7E and 7F are cross-sectional views of a single grip groove 501 having an internal protrusion 710 with two different edge configurations. In a first configuration, shown in FIG. 7E, the internal protrusion 710 extends to a flat edge 711 that will define a line of contact L1 with the cylindrical rod R1 that lengthens as the cylindrical rod R1 is urged against the edges 512, 513. Because the initial size of the line of contact L1 is small, the resistance to movement of the cylindrical rod R1 into the grip groove 510 is minimal, ensuring that a positive engagement between the cylindrical rod R1 and the internal protrusion 710 is established. In a second configuration, shown in FIG. 7F, the internal protrusion 710 has a curved edge 712 that is shaped to initially contact the cylindrical rod R1 with a longer line of contact L1, in order to increase the translational restraint of the cylindrical rod R1 upon initial contact with the edges 512, 513. The resultant strength of the restraint of the two different edge shapes 711, 712 can depend on the material properties of the cylindrical rod R1, edges 512, 513, and internal protrusion 710 and the location of the edge 711, 712 with respect to the edges 512, 513. For example, if the cylindrical rod R1 is made from a metal that is softer than the metal of the internal protrusion 710, then the edge 711, 712 can extend closer to the radius of the edges 512, 513 (i.e., the expected location of the cylindrical rod R1), such that the cylindrical rod R1 first contacts the edge 711, 712 and the edge 711, 712 is driven into the surface of the cylindrical rod R1 as the cylindrical rod R1 interfaces with the edges 512, 513.

Figure 8A:
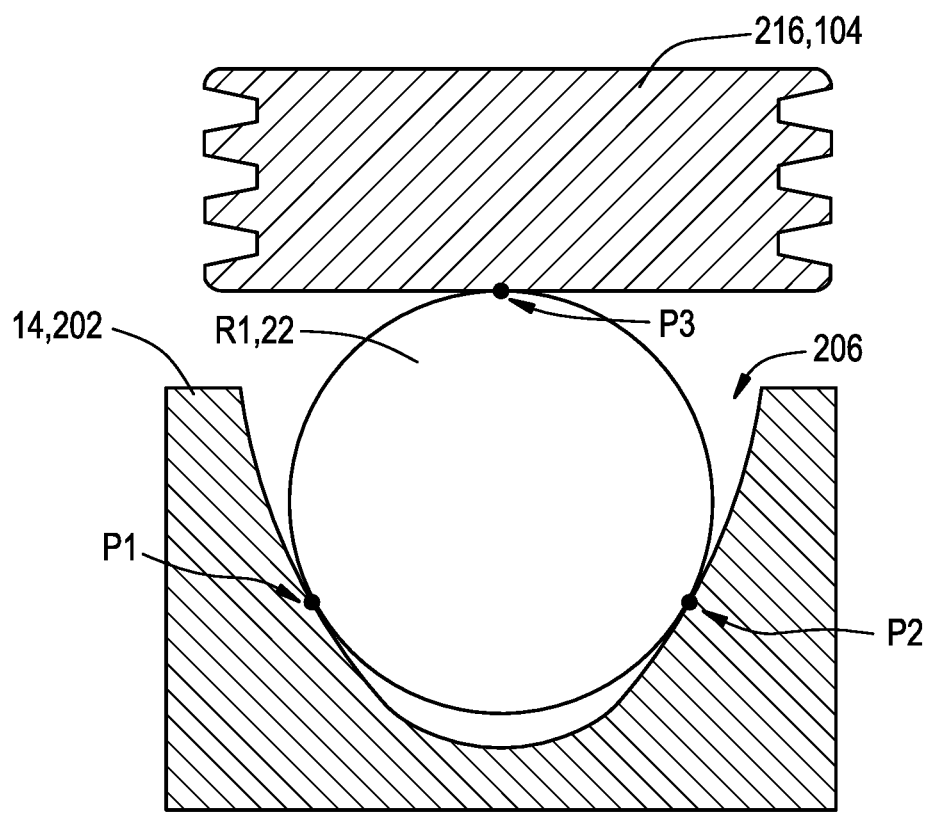
FIG. 8A is a cross-sectional view of a prior art rod-receiving recess.

FIG. 8A is a cross-sectional view of a prior art rod-receiving recess 206 of, for example, a receiver member 14 of a bone anchor assembly 10 or a body 202 of a connector 200. A cylindrical rod R1 is disposed in the rod-receiving recess 206 and contacts the inner surface of the rod-receiving recess 206 at two points P1, P2 along the axis of the rod-receiving recess 206. A locking element or set screw 104, 216 contacts the cylindrical rod R1 at point P3 and applies force to urge the cylindrical rod R1 into the rod-receiving recess 206 and against the two points P1, P2.

Figure 8B:
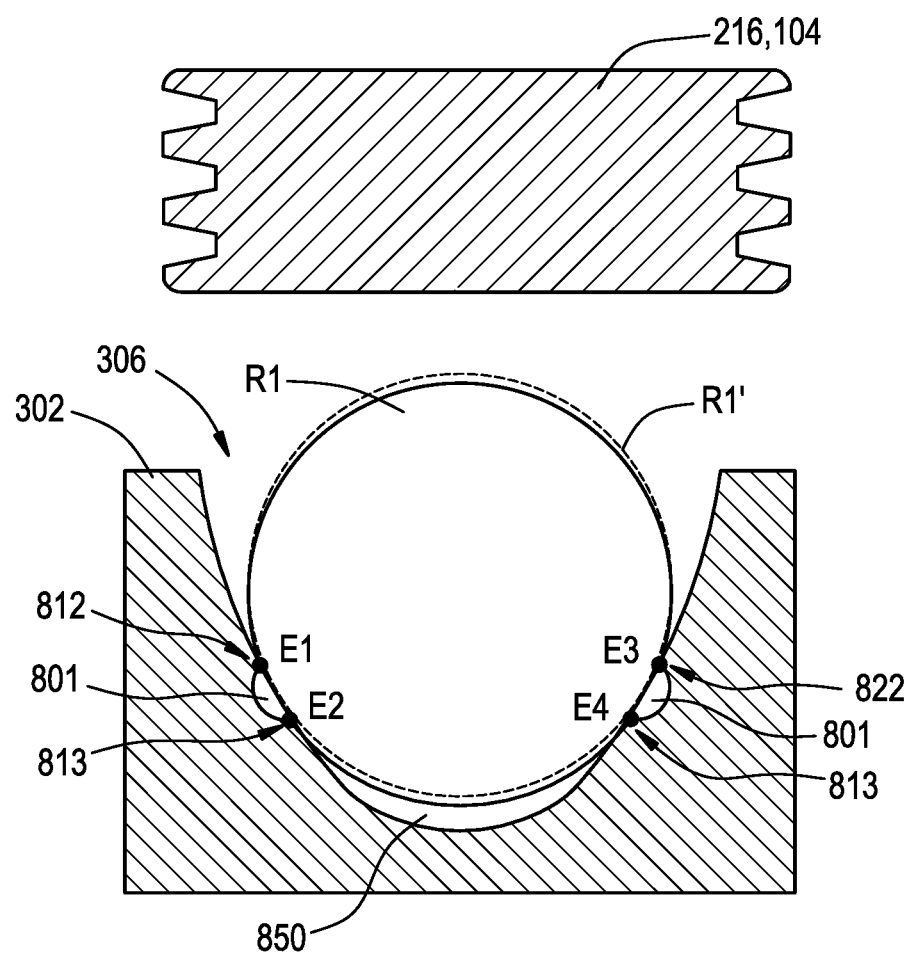
FIG. 8B is a cross-sectional view of one embodiment of a rod-receiving recess with two grip grooves.
Figure 8C:
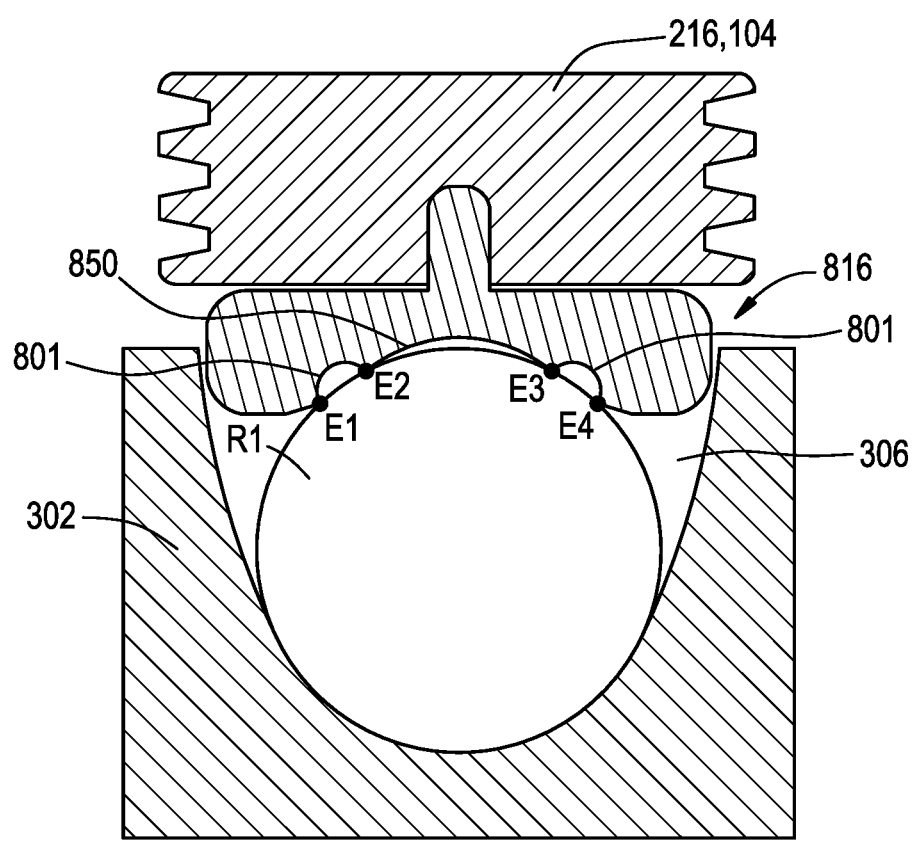
FIG. 8C is a cross-sectional view of one embodiment of a rod-receiving recess and a rod engagement element with two grip grooves.
Figure 8D:
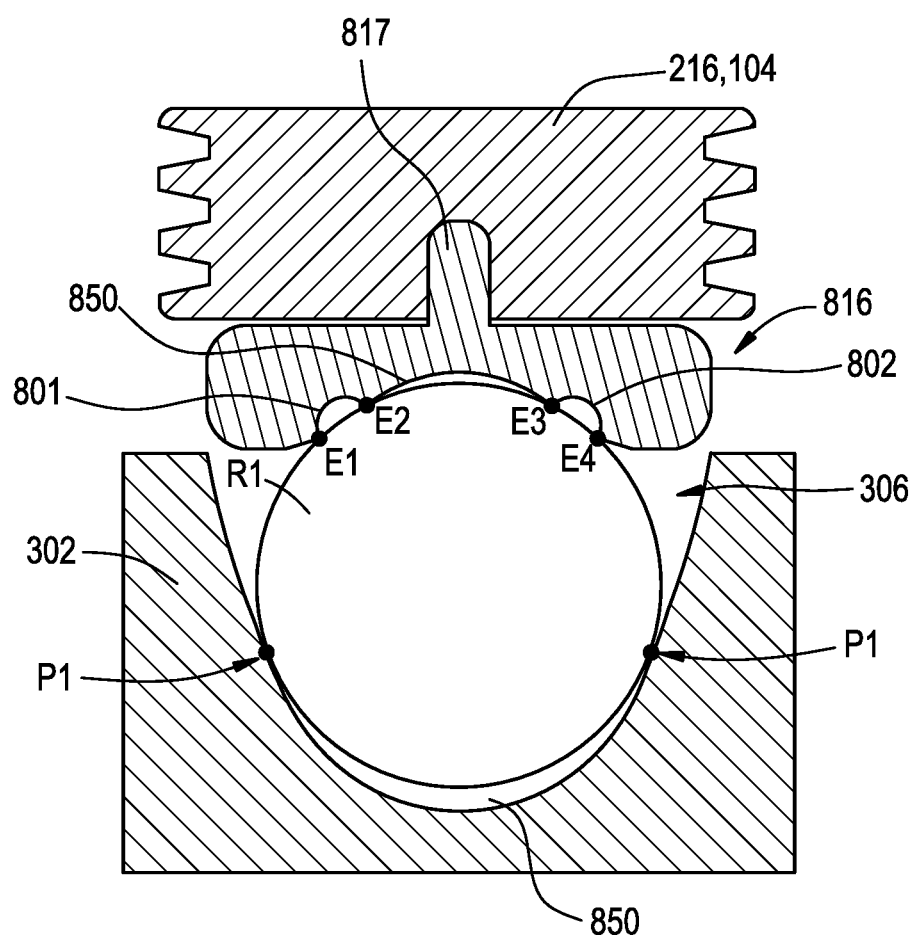
FIG. 8D is a cross-sectional view of an alternative embodiment of a rod-receiving recess and a rod engagement element with two grip grooves.

FIG. 8B is a cross-sectional view of a rod-receiving recess 306 with two grip grooves 801 formed as parallel recesses in the inner surface of the rod-receiving recess 306. FIG. 8B shows a cylindrical rod R1 disposed in the rod-receiving recess 306 and engaged with the edges 812, 813 of the grip grooves 801. A threaded locking element or set screw 104, 216 is arranged to secure the cylindrical rod R1 in the rod-receiving recess 306 by applying a force to the cylindrical rod R1 to urge the cylindrical rod R1 against the edges 812, 813 of the grip grooves 801. FIG. 8B also illustrates the position of the cylindrical rod R1 would be in the rod-receiving recess 306 if the grip grooves 801 were missing, which is shown as R1'. The difference between R1' and the position of the cylindrical rod R1 with the grip grooves 801 is due to the grip grooves 801 defining edges 812, 813 along the inner surface of the rod-receiving recess 306 at four locations with approximately the same radius from an central axis of the rod-receiving recess 306 as the cylindrical rod R1, which thereby permits the central axis of the cylindrical rod R1 to be concentric with the axis defined by the equal radius location of the edges 812, 813. Said otherwise, the grip grooves 801 are positioned to allow the cylindrical rod R1 to rest against all 4 edges 812, 813 when urged into the rod-receiving recess 306 by the locking element or set screw 104, 216. In some instances, the rod-receiving recess 306 defines a pocket or gap 850 below the designed position of the cylindrical rod R1 (as determined by the grip grooves 801), in order to allow additional urging of the cylindrical rod R1 into the rod-receiving recess 306 by the set screw 104, 216 to result in increased pressure on the edges 812, 813.

FIGS. 8C and 8D illustrate embodiments where the grip grooves 801 are positioned on an insert 816 that is driven against the cylindrical rod R1 in the rod-receiving recess 306. The insert 816 is driven by set screw 104, 216 against the cylindrical rod R1, but does not rotate with the set screw 104, 216 because the insert 816 is shaped to extend the grip grooves 801 along a length of the cylindrical rod R1. The insert 816 can include a peg 817 to be received by the set screw 104, 216 in order to couple the grooves 801 with the body 302 (into which the set screw 104, 216 is threaded, not shown) to allow the body 302 to oppose rotation of the cylindrical rod R1 via the cylindrical rod's R1 engagement with the grip grooves 801. FIG. 8C shows the rod-receiving recess 306 having a circular section to provide surface contact with the cylindrical rod R1 to oppose the force of the insert 816, and FIG. 8D shows the rod-receiving recess 306 having a tapered closed end with a gap 850 providing two lines of contact P1, P2 with the cylindrical rod R1 to oppose the force of the insert 816.

Figure 9:
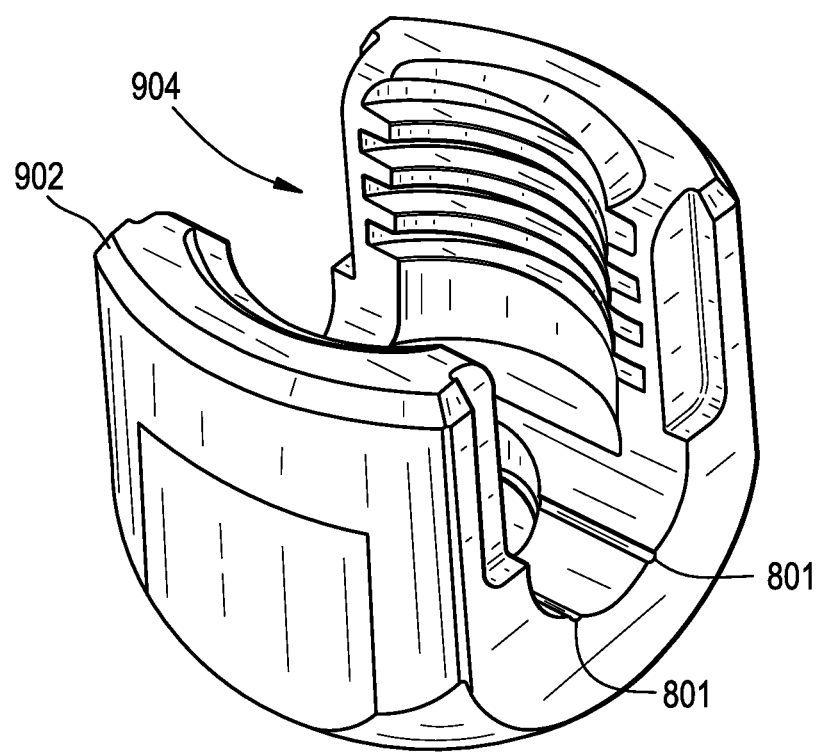
FIG. 9 is a perspective view of one embodiment of a receiving member having a rod-receiving recess with two grip grooves.
Figure 10:
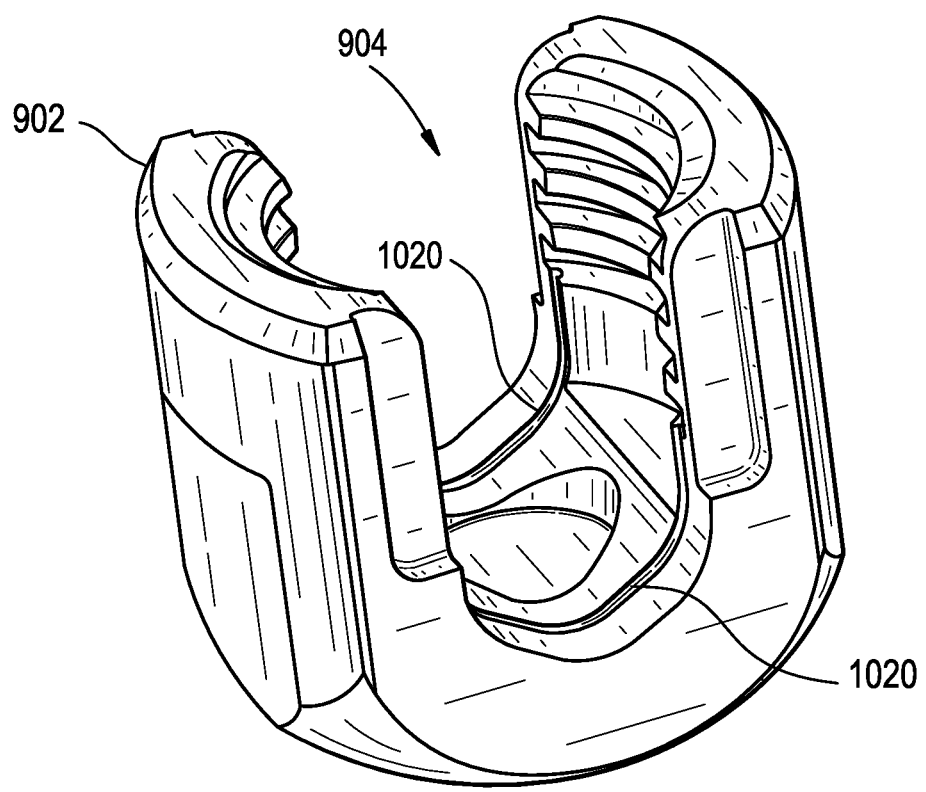
FIG. 10 is a perspective view of one embodiment of a receiving member having a rod-receiving recess with two circumferential grooves.

FIG. 9 is a perspective view of a receiving member 902 having a rod-receiving recess 904 with two grip grooves 801 formed therein. FIG. 10 is a perspective view of a receiving member 902 having a rod-receiving recess 904 with two circumferential grooves 1020 cut into the rod-receiving recess 904 perpendicular to the central longitudinal axis of the receiving recess 904.

Figure 11A:
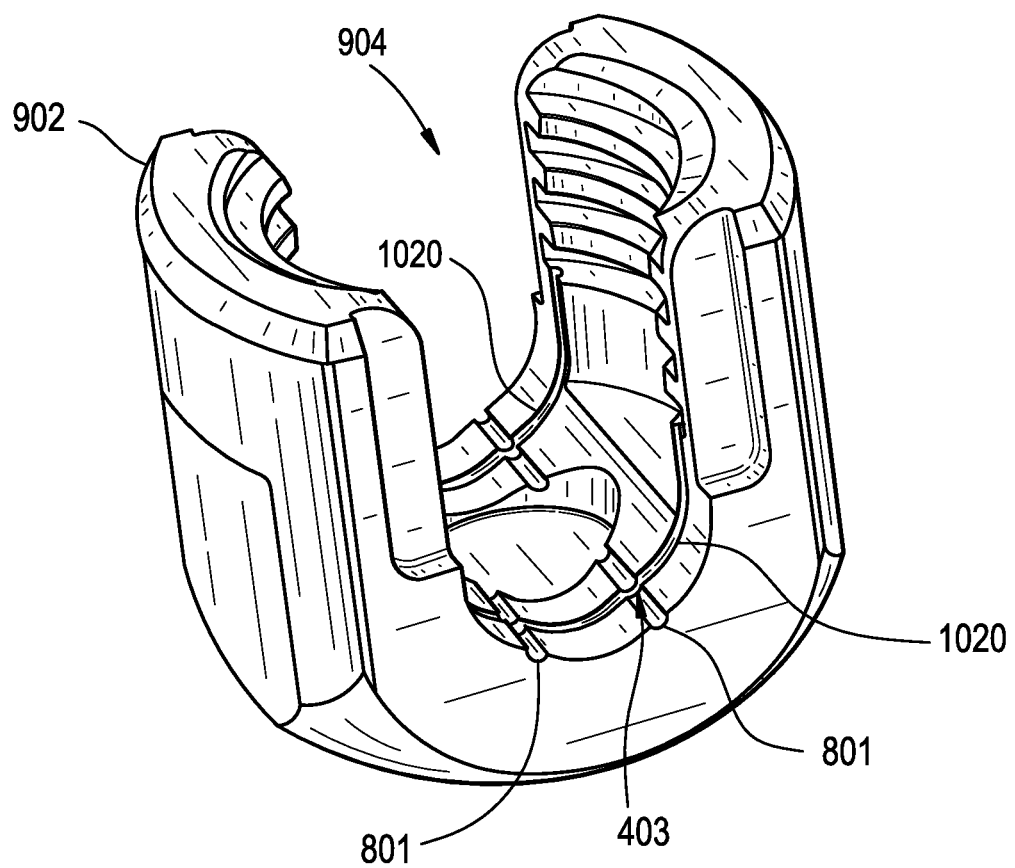
FIGS. 11A and 11B are perspective views of one embodiment of a receiving member having a rod-receiving recess with two segmented grip grooves formed by the intersection of two grip grooves and two circumferential grooves.
Figure 11B:
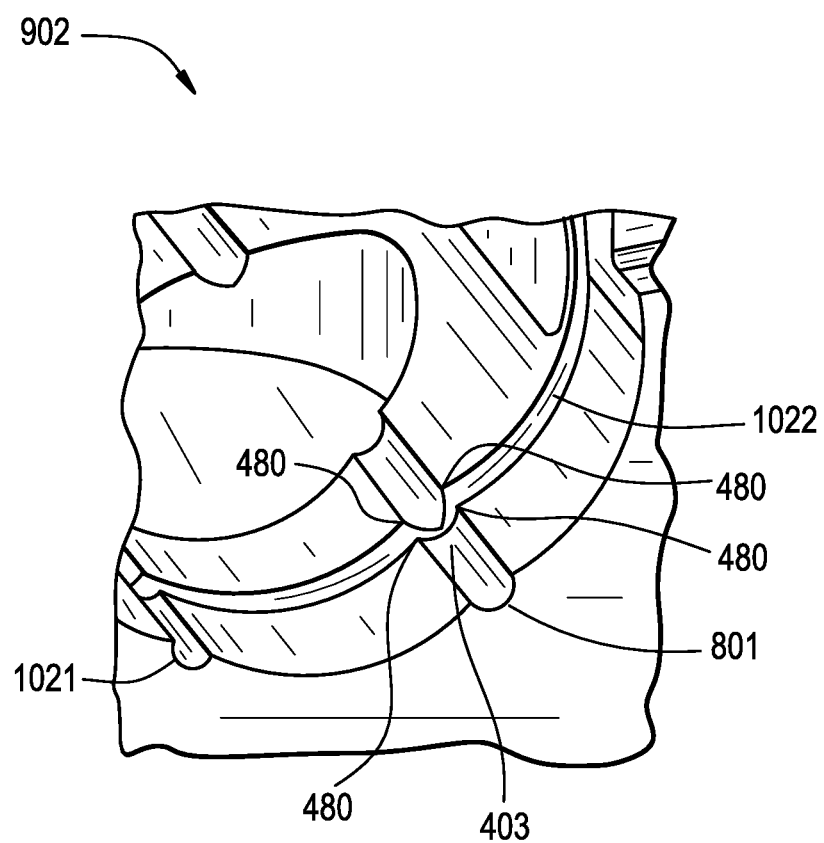
Figure 12:
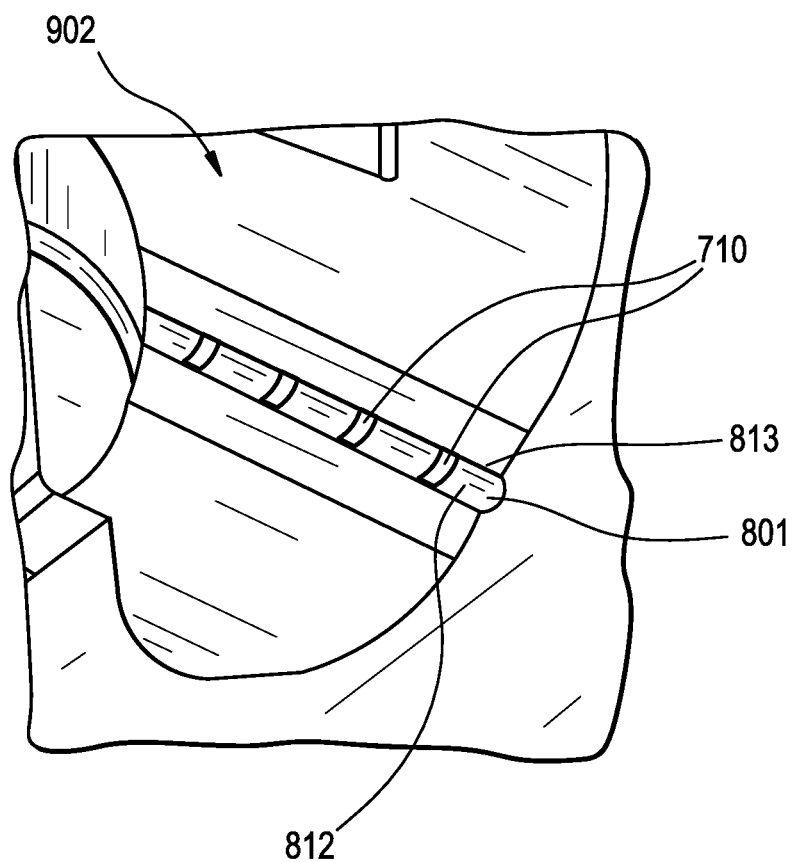
FIG. 12 is a perspective view of one embodiment of a receiving member having a rod-receiving recess with two grip grooves having multiple internal protrusions.

FIGS. 11A and 11B are perspective views of a receiving member 902 having a rod-receiving recess 904 with two segmented grip grooves 403 formed therein by the intersection of two grip grooves 801 and two circumferential grooves 1020. FIG. 11B shows the point edges 480 created in by the segmented grip grooves 403. FIG. 12 is a perspective view of a receiving member 902 having a rod-receiving recess 906 with a grip groove 801 having multiple internal protrusions 710 formed therein. The receiving member 902 and rod-receiving recess 904 of FIGS. 9-11B could be a body 302 of a connector 300, for example, or a receiver member 14 of a bone anchor assembly 10, or any other implant configured to be secured to a rod, cable, or other spinal fixation element.

Figure 13:
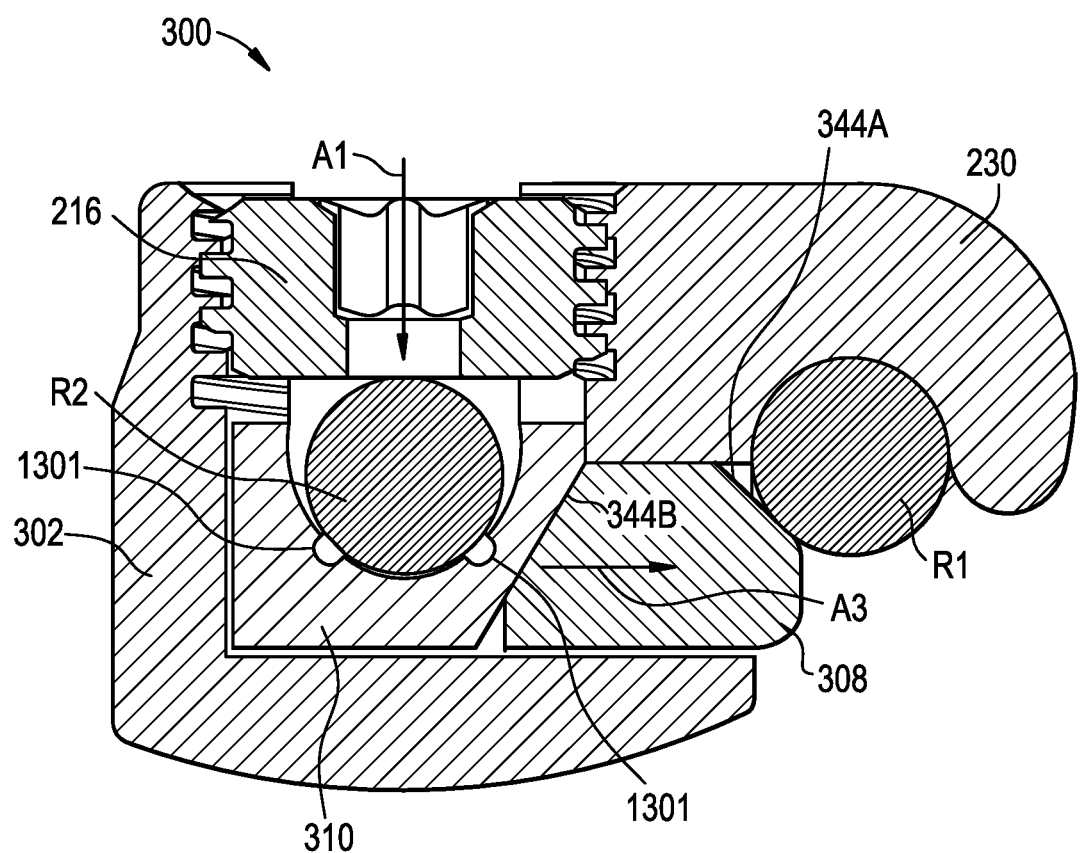
FIG. 13 is cross-sectional view of one embodiment of a connector with a rod-receiving recess having two grip grooves.

FIG. 13 is an illustration of a connector 300 with a saddle 301 that defines a rod-receiving recess with grip grooves 1301. In the connector 300 of FIG. 13, the cylindrical rod R1 is secured to the receiving member 14 by being engaged with a rod-receiving recess formed by an inner surface the saddle 301, and the inner surface of the saddle 60 includes two grip grooves 1301 configured to grip the cylindrical rod R1 when the locking screw 216 applies a force on the cylindrical rod R1 to urge the cylindrical rod R1 into the grip grooves 1301.

Figure 14:
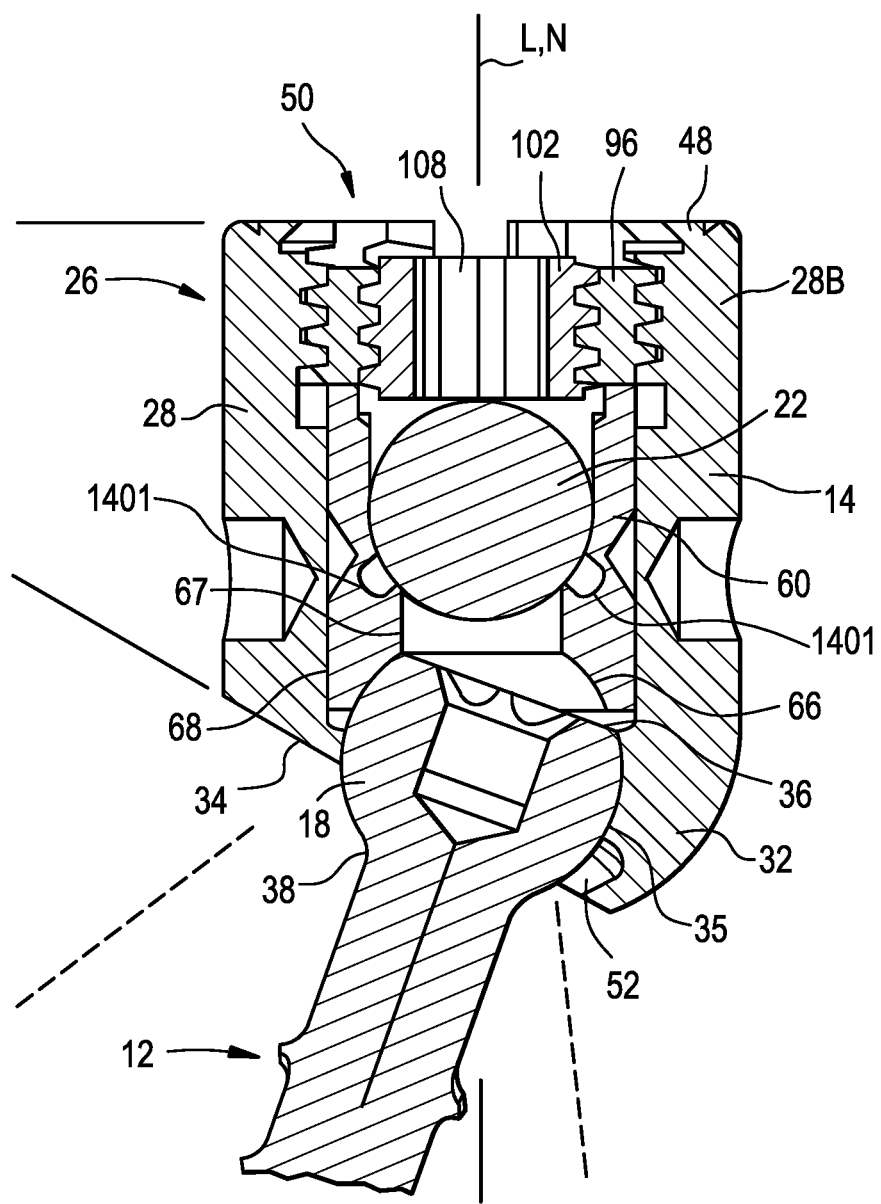
FIG. 14 is cross-sectional view of one embodiment of a bone anchor assembly with a compression member forming a rod-receiving recess and a rod engagement element with two grip grooves.

FIG. 14 is an illustration of a bone anchor assembly 10 with a compression member 60 that defines a rod-receiving recess with grip grooves 1401. In the bone anchor assembly of FIG. 14, the cylindrical rod R1 is secured to the receiver member 14 by way of contact with a compression member 60 disposed in the receiver member, where an inner surface of the compression member 60 that forms the rod-receiving recess includes the grip grooves 1401 that contact the cylindrical R1. In operation, the inner set screw 102 applies a force to the cylindrical rod R1 to urge that cylindrical rod R1 into the grip grooves 1401.

Figure 15:
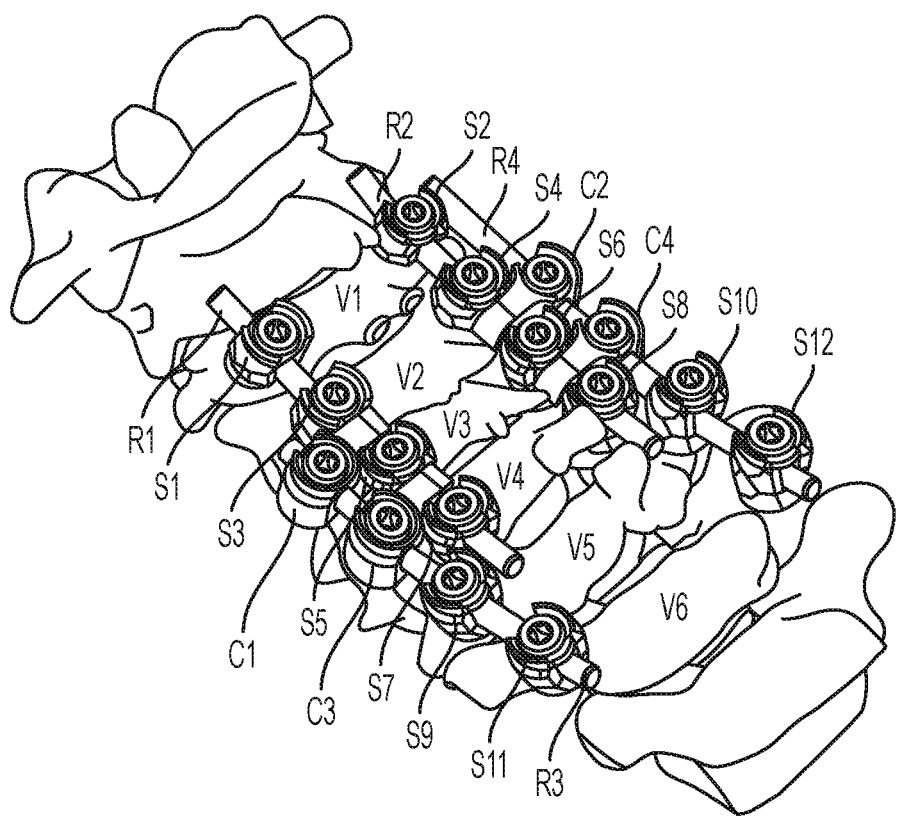
FIG. 15 is a perspective view of a human spine with a fixation system attached thereto.

FIG. 15 is a perspective view of a human spine with a fixation system attached thereto.

An exemplary method of using the bone anchors and connectors disclosed herein is described below. In some instances, the bone anchors and connectors are each secured to one or two rods in order to, for example, bridge between constructs in the cervical and thoracic regions of a patient's spine. The bone anchors and connectors can be secured to the rods using rod-receiving recesses with grip grooves in order to increase resistance to movement of the rods, connectors, ad bone anchors, relative to one another.

The procedure can begin by forming an open or percutaneous incision in the patient to access a target site. The target site can be one or more vertebrae, a long bone or multiple portions of a long bone, or any other bone or non-bone structure of the patient. As shown in FIG. 15, the target site can be multiple vertebrae in the patient's cervical and thoracic spine.

Bone anchors can be driven into one or more of the vertebrae and spinal rods can be attached thereto using known techniques. In the illustrated example, bilateral spinal rods R1, R2 are coupled to four adjacent vertebrae V1-V4 using eight bone anchors S1-S8. In addition, bilateral rods R3, R4 are coupled to the next two adjacent vertebrae V5-V6 using four bone anchors S9-S12. The rods R1, R2 can be connected to the rods R3, R4, respectively, using four connectors C1-C4 of the type described herein (e.g., connector 300) and the bone anchors S1-S8 can be connected to the rods R1-R4 using receivers of the type described herein (e.g., receiver 902).

As shown, the low-profile nature of the connectors C1-C4 can allow them to be installed at adjacent vertebral levels on the same rod (e.g., between V2/V3 and between V3/V4). As also shown, the connectors C1-C4 can connect to the rods R1, R2 between bone anchors installed in adjacent vertebral levels.

The connectors C1-C4 can receive the rods in respective rod-receiving recesses, with the rod-receiving recesses having grip grooves to secure the connector to the rods R1, R2, thereby providing improved rotational and, in some instances, axial restraint of motion of the rods R1, R2 relative to the connectors.

The connectors C1-C4 can include independent locking features such that they can be locked to the rods R1, R2 prior to being locked to the rods R3, R4 or vice versa.

The connectors C1-C4 can include single-step locking features such that they can be simultaneously locked to their respective rods. For example, connector C1 can be simultaneously locked to rods R1 and R3.

All of the rods R1-R4, the connectors C1-C4, and the bone anchors S1-S12 can be installed in a single procedure.

Alternatively, the rods R1, R2 and the bone anchors S1-S8 may have been installed in a previous procedure, and the current procedure can be a revision procedure in which the rods R3, R4, the connectors C1-C4, and the bone anchors S9-S12 are installed to extend the previously-installed construct to additional levels.

The connectors C1-C4 can be attached to position the rods R1-R4 such that they are substantially parallel to one another and substantially lie in a common coronal plane as shown. The connectors C1-C4 can also be rotated 90 degrees from the orientation shown to position the rod pairs R1, R3 and R2, R4 such that they substantially lie in respective common sagittal planes.

The above steps can be repeated to install additional rods and/or connectors at the same or at different vertebral levels. Final tightening or other adjustment of the construct can be performed and the procedure can be completed using known techniques and the incision closed.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

While the methods illustrated and described herein generally involve attaching spinal rods to multiple vertebrae, it will be appreciated that the connectors and methods herein can be used with various other types of fixation or stabilization hardware, in any bone, in non-bone tissue, or in non-living or non-tissue objects. The connectors disclosed herein can be fully implanted, or can be used as part of an external fixation or stabilization system. The devices and methods disclosed herein can be used in minimally-invasive surgery and/or open surgery.

The devices disclosed herein and the various component parts thereof can be constructed from any of a variety of known materials. Exemplary materials include those which are suitable for use in surgical applications, including metals such as stainless steel, titanium, or alloys thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

Although specific embodiments are described above, it should be understood that numerous changes may be made within the spirit and scope of the concepts described.

The invention claimed is:

1. An implant, comprising:
a body having a rod-receiving recess, the body having first and second sides defining opposing first and second lateral openings to the rod-receiving recess, the rod-receiving recess defining a central longitudinal rod axis extending between the first and second lateral openings of the first and second sides, wherein at least a portion of the rod-receiving recess is formed by an inner surface of the implant, the inner surface defining two grip grooves extending parallel to each other and the central longitudinal rod axis,
wherein each grip groove defines two edges where the grip groove intersects the inner surface, the four edges of the two grip grooves together defining a circular radius about the central longitudinal rod axis; and
a retaining member configured to move with respect to the body, exert a force against a rod in the rod-receiving recess that is perpendicular to the central longitudinal rod axis, and engage the rod against the four edges of the two grip grooves,
wherein the engagement of the four edges of the grip grooves against the rod serves to restrain rotational movement of the rod about the central longitudinal rod axis, and
wherein the inner surface defines an initial seating position for a rod in the rod-receiving recess before the force is exerted against the rod by the retaining member, the rod having a radius sized to contact all four edges of the two grip grooves,
wherein the initial seating position is configured to have the rod contact the four edges before contacting a region of the inner surface between the two grip grooves, the region extending from one of the two grip grooves to another of the two grip grooves.

2. The implant of claim 1, wherein the region of the inner surface between the two grip grooves is sized and positioned to allow the force against the rod in the rod-receiving recess to permit deflection of at least one of one or more of the four edges or the rod where one or more of the four edges engage the rod, the deflection causing movement of the rod towards the region.

3. The implant of claim 2, wherein the region of the inner surface between the two grip grooves is positioned a distance away from the central longitudinal rod axis that is larger than a radius of the rod.

4. The implant of claim 1, wherein the grip grooves extend along an entire length of the inner surface of the rod-receiving recess in the direction of the central longitudinal rod axis.

5. The implant of claim 1, wherein the grip grooves are positioned opposite the retaining member with respect to the central longitudinal rod axis.

6. The implant of claim 1, wherein the rod-receiving recess defines an open end sized to accept the rod and a closed end sized to contact the rod, wherein the grip grooves are arranged symmetrically about an axis extending from the open end to the closed end.

7. The implant of claim 1, wherein the body of the implant defines the inner surface forming the rod-receiving recess.

8. The implant of claim 1, wherein the intersection between the grip grooves and the inner surface defines sharp edges.

9. The implant of claim 1, wherein the implant comprises a connector and the rod-receiving recess is a first rod-receiving recces, the body defining a second rod-receiving recess with one or both of the first and second rod-receiving recesses having the two grip grooves, the body having proximal and distal ends that define a proximal-distal axis extending therebetween;
wherein the retaining member is slidably disposed within a tunnel formed in the body and configured to translate with respect to the body along a rod pusher axis.

10. The implant of claim 9, wherein the second rod-receiving recess is defined by a pair of spaced apart arms of the body.

11. The connector of claim 9, wherein the first rod-receiving recess is open in a distal direction and wherein the second rod-receiving recess is open in a proximal direction.

12. The connector of claim 9, wherein the rod pusher axis is substantially perpendicular to the proximal-distal axis.

13. The connector of claim 9, further comprising a set screw threadably received in the body to lock a first rod within the first rod-receiving recess and to lock a second rod within the second rod-receiving recess.

14. The implant of claim 1, wherein the implant comprises a bone anchor assembly, the body comprises a receiver member of the bone anchor assembly, and the retaining member comprises a set screw or locking element.

15. An implant, comprising:
a body having a rod-receiving recess, the body having first and second sides defining openings to the rod-receiving recess, the rod-receiving recess defining a central longitudinal rod axis extending between the openings of the first and second sides;
a grip insert configured to be positioned in an open end of the receiving recess and defining an inner surface for contacting a rod disposed in the rod-receiving recess, the inner surface defining two grip grooves extending parallel to each other and the central longitudinal rod axis, wherein each grip groove defines two edges where the grip groove intersects the inner surface, the four edges of the two grip grooves together defining a circular radius about the central longitudinal rod axis; and
a retaining member configured to move with respect to the body, exert a force against a rod in the rod-receiving recess, and engage the four edges of the grip against the rod, wherein the engagement of the four edges of the grip grooves against the rod serves to restrain rotational movement of the rod about the central longitudinal rod axis wherein the inner surface defines a seating position for a rod in the rod-receiving recess before the force is exerted against the rod by the retaining member, the rod having a radius sized to contact all four edges of the two grip grooves, wherein the initial seating position is configured to have the rod contact the four edges before contacting a region of the inner surface between the two grip grooves, the region extending from one of the two grip grooves to another of the two grip grooves.

16. A connector implant, comprising:

a body having a first rod-receiving recess, a second rod-receiving recess, and a tunnel in the body that extends from a closed end of the first rod-receiving recess towards the second rod-receiving recess, the body having a wing portion that extends away from the first rod-receiving recess, wing portion having an inner surface that defines the second rod-receiving recess, the second rod-receiving recess defining a central longitudinal rod axis, and the inner surface defining two grip grooves extending parallel to each other and the central longitudinal rod axis; and a rod pusher slidably displaced in the tunnel, the rod pusher having a first bearing surface and a second bearing surface, the second bearing surface adjacent to the second rod-receiving recess, the first bearing surface configured to receive a force from a rod disposed in the first-rod receiving recess such that movement of a rod in the first rod-receiving recess towards the closed end of the first rod-receiving recess translates the rod pusher in the tunnel toward the second rod-receiving recess such that the second bearing surface is advanced towards the two grip grooves of the second rod-receiving recess, wherein the wing portion and the second bearing surface of the rod pusher define an opening to the second rod-receiving recess therebetween, wherein each grip groove defines two edges where the grip groove intersects the inner surface, the four edges of the two grip grooves together defining a circular radius about the central longitudinal rod axis; and wherein the rod pusher is configured to move in the tunnel to exert a force against a rod in the second rod-receiving recess and engage the rod against the four edges of the two grip grooves, wherein the engagement of the four edges of the grip grooves against the rod serves to restrain rotational movement of the rod about the central longitudinal rod axis, and wherein the inner surface defines a seating position for a rod in the second rod-receiving recess before the force is exerted against the rod by the retaining member, the rod having a radius sized to contact all four edges of the two grip grooves, wherein the initial seating position is configured to have the rod contact the four edges before contacting a region of the inner surface between the two grip grooves, the region extending from one of the two grip grooves to another of the two grip grooves.

17. The implant of claim 16, wherein the region of the inner surface between the two grip grooves is sized and positioned to allow the force against the rod in the second rod-receiving recess to permit deflection of at least one of one or more of the four edges or the rod where one or more of the four edges engage the rod, the deflection causing movement of the rod towards the region.

18. A connector implant, comprising:

a body having a first rod-receiving recess, a second rod-receiving recess, and a tunnel in the body that extends from a closed end of the first rod-receiving recess towards the second rod-receiving recess, the body having a wing portion that extends away from the first rod-receiving recess, wing portion having an inner surface that defines the second rod-receiving recess, the second rod-receiving recess defining a central longitudinal rod axis; and a rod pusher slidably displaced in the tunnel, the rod pusher having a first bearing surface and a second bearing surface, the second bearing surface adjacent to the second rod-receiving recess, the first bearing surface configured to receive a force from a rod disposed in the first-rod receiving recess such that movement of a rod in the first rod-receiving recess towards the closed end of the first rod-receiving recess translates the rod pusher in the tunnel toward the second rod-receiving recess such that the second bearing surface is advanced towards the two grip grooves of the second rod-receiving recess, wherein the second bearing surface defines two grip grooves extending parallel to each other and the central longitudinal rod axis wherein the wing portion and the second bearing surface of the rod pusher define an opening to the second rod-receiving recess therebetween, wherein each grip groove defines two edges where the grip groove intersects the second bearing surface, the four edges of the two grip grooves together configured to define a circular radius about the central longitudinal rod axis when the second bearing surface is advanced into the second rod-receiving recess; and wherein the rod pusher is configured to move in the tunnel to exert a force against a rod in the second rod-receiving recess and engage the rod against the four edges of the two grip grooves, wherein the engagement of the four edges of the grip grooves against the rod serves to restrain rotational movement of the rod about the central longitudinal rod axis, and wherein the second bearing surface defines a seating position for a rod in the second rod-receiving recess before the force is exerted against the rod by the retaining member, the rod having a radius sized to contact all four edges of the two grip grooves, wherein the initial seating position is configured to have the rod contact the four edges before contacting a region of the inner surface between the two grip grooves, the region extending from one of the two grip grooves to another of the two grip grooves.

19. The implant of claim 18, wherein the region of the second bearing surface between the two grip grooves is sized and positioned to allow the force against the rod in the rod-receiving recess to permit deflection of at least one of one or more of the four edges or the rod where one or more of the four edges engage the rod, the deflection causing movement of the rod towards the region.

* * * * *